(12) United States Patent
Horhota et al.

(10) Patent No.: US 10,952,972 B2
(45) Date of Patent: Mar. 23, 2021

(54) THERAPEUTIC NANOPARTICLES COMPRISING A THERAPEUTIC AGENT AND METHODS OF MAKING AND USING SAME

(71) Applicant: Pfizer Inc., New York, NY (US)

(72) Inventors: Allen Thomas Horhota, Westford, MA (US); Young-Ho Song, Natick, MA (US); Ujjwal Chaitanya Joshi, Arlington, MA (US); Nicholas Jon Boylan, Shrewsbury, MA (US); Matthew John Simmons, Framingham, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/988,947

(22) Filed: May 24, 2018

(65) Prior Publication Data

US 2019/0091164 A1    Mar. 28, 2019

Related U.S. Application Data

(63) Continuation of application No. 15/241,954, filed on Aug. 19, 2016, now abandoned.

(60) Provisional application No. 62/349,377, filed on Jun. 13, 2016, provisional application No. 62/279,295, filed on Jan. 15, 2016, provisional application No. 62/242,515, filed on Oct. 16, 2015, provisional application No. 62/238,400, filed on Oct. 7, 2015, provisional application No. 62/208,361, filed on Aug. 21, 2015.

(51) Int. Cl.
| | | |
|---|---|---|
| *A61K 9/51* | (2006.01) | |
| *A61K 31/713* | (2006.01) | |
| *A61K 47/54* | (2017.01) | |

(52) U.S. Cl.
CPC .......... *A61K 9/5153* (2013.01); *A61K 31/713* (2013.01); *A61K 47/541* (2017.08)

(58) Field of Classification Search
None
See application file for complete search history.

(56) References Cited

U.S. PATENT DOCUMENTS

| | | |
|---|---|---|
| 8,986,691 B1 | 3/2015 | Clube |
| 2009/0312402 A1 | 12/2009 | Contag |
| 2010/0068285 A1 | 3/2010 | Zale |
| 2014/0308363 A1 | 10/2014 | Zale |
| 2015/0056300 A1 | 2/2015 | Dewitt et al. |
| 2015/0139906 A1 | 5/2015 | Labhasetwar et al. |
| 2017/0049709 A1 | 2/2017 | Horhota et al. |

FOREIGN PATENT DOCUMENTS

| | | |
|---|---|---|
| WO | 2005111238 | 11/2005 |
| WO | 2014066912 | 5/2014 |
| WO | 2015058111 | 4/2015 |
| WO | 2015123562 | 8/2015 |

OTHER PUBLICATIONS

Grandis, Jennifer R., et al., "Requirement of Stat3 but not Stat1 Activation for Epidermal Growth Factor Receptor-mediated Cell Growth In Vitro", Journal of Clin Invest., Oct. 1998, pp. 1385-1392, 102(7).
Gowda, Raghavendra, et al., "Nanolipolee-007, a Novel Nanoparticle-Based Drug Containing Leelamine for the Treatment of Melanoma", Molecular Cancer Therapeutics, 2014, pp. 2328-2340, 13(10).
Product Ingredient Fluoxetine Hydrocholoride; retrieved from https://www.drugbank.ca/salts/DBSALT000087 on Nov. 23, 2017 (Year 2017).
Promethazine Hydrochloride; retrieved from https://pubchem.ncbi.nlm.nih.gov/compound/promethazine_hydrochloride#section=Solubility on Nov. 23, 2017 (Year 2017).
Leelamine HCl, retrieved from https://pubchem.ncbi.nlm.nih.gov/compound/46780578#section=Computed-Properties on Nov. 23, 2017 (Year 2017).
Chlorpromazine, retrieved from https://pubchem.ncbi.nlm.nih.gov/compound/chlorpromazine#section=Top on Nov. 23, 2017 (Year 2017).
Gowda, Raghavendra, et al., "Nanolipolee-007, a Novel Nanoparticle-Based Drug Containing Leelamine for the Treatment of Melanoma", Molecular Cancer Therapeutics, 2014, pp. 1679-1689, 13(7).
Horobin, Richard et al., "A QSAR-modeling perspective on cationic transfection lipids.1.Predicting efficiency and understanding mechanisms", The Journal of Gene Medicine, 2005, pp. 1023-1034, vol. 7.
Vigneron, Jean-Pierre et al., Guanidinium-cholesterol cationic lipids: Efficient vectors for the transfection of eukaryotic cells, Proc. Nat. Acad. Sci., 1996, pp. 9682-9686, vol. 93.
Cheng, Jianjun et al., "Formulation of Functionalized PLGA-PEG nanoparticles for in vivo targeted drug delivery", Biomaterials, 2007, pp. 869-876, vol. 28.
Lupold, Shawn et al., "Identification and Characterization of Nuclease-stabilized RNA Molecules That Bind Human Prostate Cancer Cells via the Prostate-specific Membrane Antigen", Cancer Research, Jul. 15, 2012, pp. 4029-4033, vol. 62.
Drugbank data for Toremifene, downloaded from https://www.drugbank.ca/drugs/DB00539 on Mar. 19, 2017.
hariri, Waseem et al., "Nano-Targeted Delivery of Toremifene, an Estrogen Receptor-a Blocker in Prostate Cancer", Pharm Res., Mar. 12, 2015, pp. 2764-2774, vol. 32.
International Patent Application No. PCT/US2016/047799, filed Aug. 19, 2016, International Search Report and Written Opinion, dated Nov. 4, 2016, 15 pages.
International Patent Application No. PCT/US2016/047799, filed Aug. 19, 2016, International Preliminary Report on Patentability, dated Feb. 27, 2018, 6 pages.

(Continued)

*Primary Examiner* — Richard A Schnizer
(74) *Attorney, Agent, or Firm* — Mary J. Hosley

(57) ABSTRACT

The present disclosure generally relates to nanoparticles comprising an endo-lysosomal escape agent, a nucleic acid, and a polymer. Other aspects include methods of making and using such nanoparticles.

10 Claims, 32 Drawing Sheets

Specification includes a Sequence Listing.

(56) References Cited

OTHER PUBLICATIONS

Yamamoto et al., "Nanomedical system for nucleic acid drugs created with the biodegradable nanoparticle platform", Journal of Microencapsulation, vol. 29(1); pp. 54-62 (2011); XP055474755, GB, ISSN: 0265-2048, DOI: 10.3109/02652048.2011.629745.

Jin, Yignuang, et al., Colloids Surf B Biointerfaces. 126, pp. 257-264 (Dec. 31, 2014).

Perez, et al., "Uptake and intracellular traffic of siRNA dendriplexes in glioblastoma cells and macrophages", Int J Nanomed. vol. 6, pp. 2715-2728 (2011).

Ren et al., "EGFR-targeted poly(ethylene glycol)-distearoylphosphatidylethanolamine micelle loaded with paclitaxel for laryngeal cancer: preparation, characterization and in vitro evaluation", Drug Delivery, vol. 22(6); pp. 785-794 (2015).

Untreated siRNA Formulation + Doxepin

THERAPEUTIC NANOPARTICLES COMPRISING A THERAPEUTIC AGENT AND METHODS OF MAKING AND USING SAME

RELATED APPLICATIONS

This application is a continuation application under 35 U.S.C. § 120 of U.S. patent application Ser. No. 15/241,954 filed Aug. 19, 2016 which claims the benefit of U.S. Provisional Patent Application No. 62/349,377, filed on Jun. 13, 2016, and U.S. Provisional Patent Application No. 62/279,295, filed on Jan. 15, 2016, and U.S. Provisional Patent Application No. 62/242,515, filed on Oct. 16, 2015, and U.S. Provisional Patent Application No. 62/238,400, filed on Oct. 7, 2015, and U.S. Provisional Patent Application No. 62/208,361, filed on Aug. 21, 2015, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 24, 2018, is named PC45256B-SeqListing ST25.txt and is 1,993 bytes in size.

BACKGROUND

Systems that deliver certain drugs to a patient (e.g., targeted to a particular tissue or cell type or targeted to a specific diseased tissue but not normal tissue) or that control release of drugs have long been recognized as beneficial.

For example, therapeutics that include an active drug and that are, e.g., targeted to a particular tissue or cell type or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach.

Therapeutics that offer controlled release and/or targeted therapy also must be able to deliver an effective amount of drug, which is a known limitation in other nanoparticle delivery systems. For example, it can be a challenge to prepare nanoparticle systems that have an appropriate amount of drug associated with each nanoparticle, while keeping the size of the nanoparticles small enough to have advantageous delivery properties.

Therapeutic delivery of nucleic acids such as therapeutic siRNA, mRNA or antisense require efficient and nontoxic delivery methods. However, there are significant challenges in such delivery, including, for example, degradation of nucleic acids by nucleases and/or lack of effective transport into the cell or nucleus. Nanoparticle formulations that include nucleic acids are often hindered by undesirable properties, e.g., burst release profiles and degradation of the nucleic acid.

Accordingly, a need exists for nanoparticle therapeutics and methods of making such nanoparticles that are capable of delivering nucleic acid molecules into cells, while also preventing degradation of the nucleic acid molecule.

SUMMARY

Described herein are therapeutic and/or pharmaceutically acceptable polymeric nanoparticles that include a nucleic acid and a hydrophobic counterion, and methods of making and using such nanoparticles. For example, provided herein is a pharmaceutically acceptable nanoparticle comprising a nucleic acid and a hydrophobic counter ion agent; and about 50 to about 99.75 weight percent of a diblock poly(lactic) acid-poly(ethylene)glycol copolymer or a diblock poly(lactic acid-co-glycolic acid)-poly(ethylene)glycol copolymer. The hydrophobic counter ion agent may be for example, an endosomal and/or a lysosomal disrupting agent (e.g., a endo-lysosomal disrupting agent).

Contemplated nanoparticles may include nucleic acids such as those selected from the group comprising: an antisense compound, mRNA, short interfering RNA (siRNA), double stranded RNA (dsRNA), micro-RNA (miRNA), small nucleolar RNA (sno-RNA), Piwi-interacting RNA (piRNA), and short hairpin RNA (shRNA) molecules. For example, contemplated nucleic acids may be an oligonucleotide (e.g., an antisense), an aptamer, a vector, a threose nucleic acid, a glycol nucleic acid (GNAs), and a locked nucleic acid (LNAs). In some embodiments, nanoparticles include unmodified nucleic acids.

In some aspects, nanoparticles are provided herein that include a nucleic acid and a hydrophobic counter ion agent having a log P of about 2 or more, for example, a log P of between about 2 and about 3.

It should be appreciated that a nanoparticle may comprise, one nucleic acid molecule, or a plurality of nucleic acid molecules. The plurality of nucleic acid molecules may comprise one or more types or kinds of nucleic acid molecules. For example, a nanoparticle may comprise both a miRNA and a shRNA.

BRIEF DESCRIPTION OF THE DRAWINGS

FIG. 18A depicts the relative eGFP fluorescence results as measured by the Incucyte® Live Cell Analysis System.

FIG. 18B reports the real time PCR transcription results.

DETAILED DESCRIPTION

Figure 1:
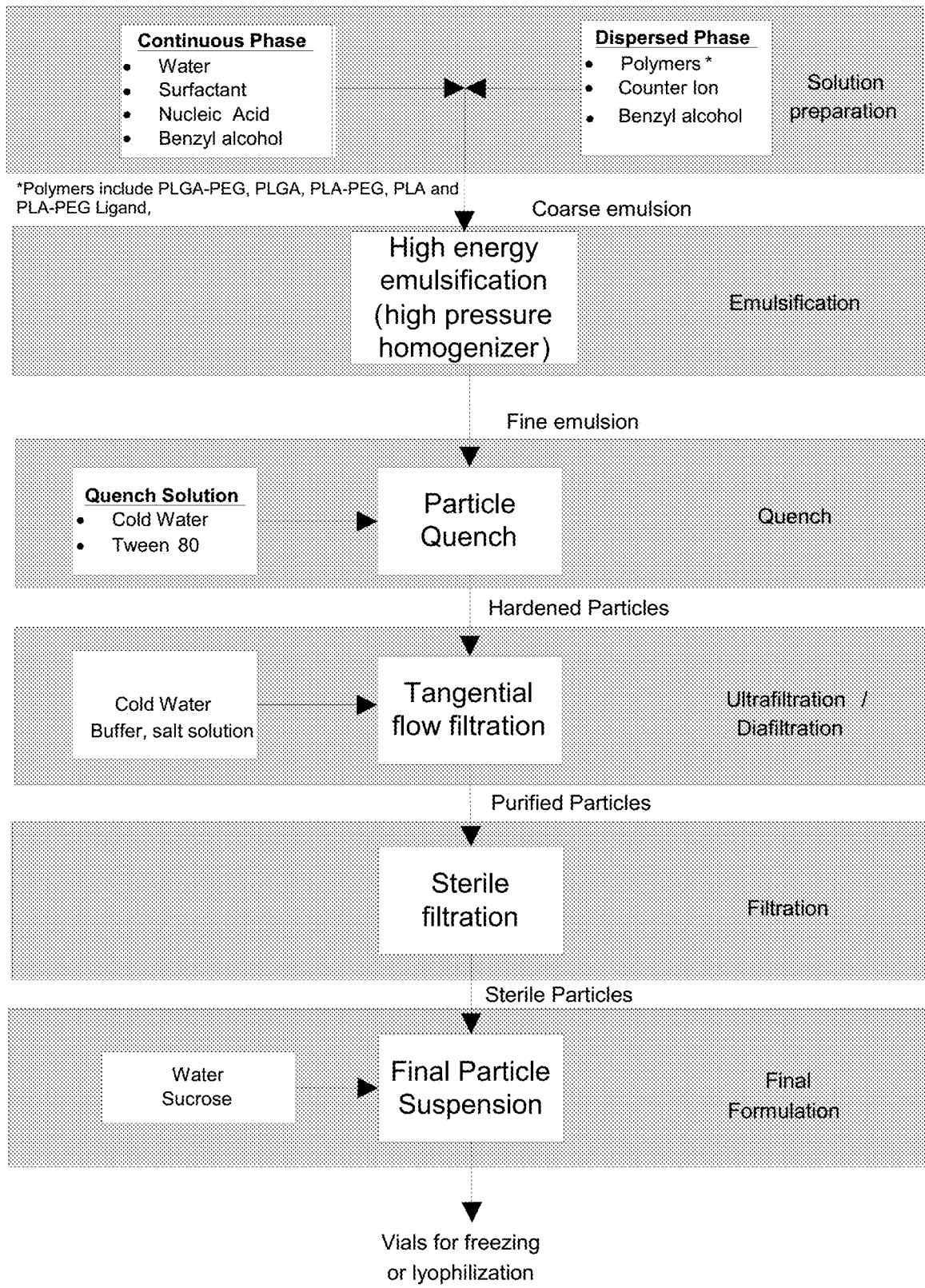
FIG. 1 is flow chart for an emulsion process for forming a disclosed nanoparticle.

Described herein are polymeric nanoparticles that include a nucleic acid, and methods of making and using such therapeutic nanoparticles. In some embodiments, a disclosed nanoparticle includes an ion-pair that includes a nucleic acid molecule and a hydrophobic counter ion, such as an endo-lysosomal disrupting agent. For example, such disclosed nanoparticles may accomplish effective transfection. Furthermore, in certain embodiments, nanoparticles that include and/or are prepared in the presence of a hydrophobic counter ion agent, such as an endo-lysosomal disrupting agent, may exhibit improved nucleic acid molecular integrity. For example, disclosed nanoparticles that include a nucleic acid may substantially prevent nucleic acid degradation in addition to achieving effective transfection, e.g., once administered to a patient.

Without wishing to be bound by any theory, it is believed that a disclosed nanoparticle that includes at least one nucleic acid has significantly improved nucleic acid integrity and/or -transfection from the formation of an ion-pair with a hydrophobic counter ion agent, such as an endo-lysosomal disrupting agent. It should be appreciated that the term "ion-pair" is not to be limited to a 1:1 ratio, but instead refers to the ions of opposite charges, in any ratio, to be attracted to one another. For example, a nucleic acid molecule with eight negative charges may be "paired" with eight positively charged molecules. Thus, as used herein, an ion-pair is a pair of oppositely charged ions held together by Coulombic attraction. Ion-pair formation, as contemplated herein, can result in nanoparticles having for example, increased drug loading. Slower release of the nucleic acid from the nanoparticles may also occur, for example in some embodiments, due to a decrease in the nucleic acid's solubility in aqueous solution. Furthermore, complexing the nucleic acid with large hydrophobic counter ions may slow diffusion of the nucleic acid within the polymeric matrix. It should be noted that the ion-pair may also be referred to herein as a complex. Advantageously, ion-pair formation occurs without the need for covalent conjugation of the hydrophobic group to the therapeutic agent.

Without wishing to be bound by any theory, it is believed that the strength of the ion-pair impacts the drug load and release rate of the contemplated nanoparticles. For example, the strength of the ion-pair may be increased by increasing the magnitude of the difference between the $pK_a$ of the nucleic acid and the $pK_a$ of the hydrophobic counter ion agent, such as an endo-lysosomal disrupting agent, as discussed in more detail below. Also, without wishing to be bound by any theory, it is believed that the conditions for ion pair formation impact the drug load and release rate of the contemplated nanoparticles.

Nanoparticles disclosed herein include one, two, three or more biocompatible and/or biodegradable polymers. For example, a contemplated nanoparticle may include about 35 to about 99.75 weight percent, in some embodiments about 50 to about 99.75 weight percent, in some embodiments about 50 to about 99.5 weight percent, in some embodiments about 50 to about 99 weight percent, in some embodiments about 50 to about 98 weight percent, in some embodiments about 50 to about 97 weight percent, in some embodiments about 50 to about 96 weight percent, in some embodiments about 50 to about 95 weight percent, in some embodiments about 50 to about 94 weight percent, in some embodiments about 50 to about 93 weight percent, in some embodiments about 50 to about 92 weight percent, in some embodiments about 50 to about 91 weight percent, in some embodiments about 50 to about 90 weight percent, in some embodiments about 50 to about 85 weight percent, in some embodiments about 60 to about 85 weight percent, in some embodiments about 65 to about 85 weight percent, and in some embodiments about 50 to about 80 weight percent of one or more block copolymers that include a biodegradable polymer and poly(ethylene glycol) (PEG), and about 0 to about 50 weight percent of a biodegradable homopolymer.

The disclosed nanoparticles may include a nucleic acid. The term nucleic acid, can include any compound and/or substance that is or can be incorporated into an oligonucleotide chain. Exemplary nucleic acids for use in accordance with the disclosed nanoparticles include, but are not limited to, one or more of DNA, RNA, hybrids thereof, RNAiinducing agents, RNAi agents, antisense RNAs, ribozymes, catalytic DNA, RNAs that induce triple helix formation, aptamers, and vectors. The nucleic acids may be single strand (sense or antisense), or double strand. The nanoparticles may include small nucleic acid molecules such as such as short interfering RNA (siRNA), double stranded RNA (dsRNA), micro-RNA (miRNA), small nucleolar RNA (snoRNA), Piwi-interacting RNA (piRNA), and short hairpin RNA (shRNA) molecules. Exemplary nucleic acids include ribonucleic acids (RNAs), transfer RNA (tRNA), deoxyribonucleic acids (DNAs), threose nucleic acids (TNAs), glycol nucleic acids (GNAs), locked nucleic acids (LNAs) or a hybrid thereof. In other embodiments, messenger RNAs (mRNAs) or noncoding RNA (ncRNA) may be incorporated into the nanoparticle. Further, the nucleic acid may be an antagomir, an antimir, or a U1 adaptor. In an embodiment provided herein is a nanoparticle that includes an antisense oligonucleotide (e.g., an antisense that includes at least one phsphorothioate internucleoside linkage such as an antisense compound complementary to a nucleic acid encoding human STAT3, (e.g., complementary to a segment of GENBANK accession No. NM 139276.2, such as to nucleobases 3016-3031), and/or such as those disclosed in WO2014070868, hereby incorporated by reference. For example, provided herein is a sequence comprising CTATTTGGATGTCAGC (SEQ ID NO: 1) having phosphorothioate internucleoside linkages and where each cytosine is a 5-methylcytosine and each of the nucleosides 1-3 and 14-16 include a cEt moiety.

Some embodiments of disclosed nanoparticles include unmodified nucleic acids. In other embodiments, the nucleic acids are modified. Modifications can include any modification known in the art, including but not limited to modification of the phosphodiester backbone, modification at the ribose 2'OH group, and modification of the ribose ring and nucleoside base. For example, modification of the phosphate backbone can include phosphorothioate (PS) modification, where a non-bridging phosphate oxygen is replaced with sulfur. Additionally, other modifications include phosphorodithioates and phosphonoacetates. See U.S. Pat. Nos. 6,143,881, 5,587,361 and 5,599,797, which are incorporated by reference. Other modifications include 2'O-methyl (2'OMe), 2'Fluoro (2'F), 2'Methoxyethyl (2'-O-MOE), 2'Fluorarabino (FANA), 2'-H, 2'-Thiouracil, locked nucleic acid (LNA), bridged nucleic acid (BNA), ethylene-bridged nucleic acid (ENA), hexitol nucleic acid (HNA), altritol nucleic acid (ANA), cyclohexene nucleic acid (CeNA), unlocked nucleic acid (UNA), 4'Thio (4'-S), and 3'inverted abasic end cap. In some embodiments, a nucleic acid may be modified by substituting a native phosphodiester linkage with a boranophosphate (PB) linkage, a phosphonoacetate (Pac) linkage or a thiophosphonoacetate backone linkage. In some embodiments, the nucleic acid may include more than one modification. In some embodiments, the nucleic acid may comprise more than two modifications.

In some embodiments, a nucleic acid can be selected from the group consisting of single strand, double strand, or triple strand nucleic acids. Examples of single strand nucleic acid molecules that have biologic activity, e.g., mediate alteration of gene expression, include antisense nucleic acid molecules, enzymatic nucleic acid molecules or ribozymes, and 2-5-oligoadenylate nucleic acid molecules. Examples of triple strand nucleic acid molecules that have biologic activity to mediate alteration of gene expression include triplex forming oligonucleotides. Examples of double strand nucleic acid molecules that have biologic activity to mediate alteration of gene expression include dsRNA and siRNA. For example, interferon mediated induction of protein kinase PKR may be activated in a non-sequence specific manner by long double stranded RNA (see, for example, Wu and Kaufman, 1997, J. Biol. Chem., 272, 1921-6). This pathway may hares a common feature with the 2,5-linked oligoadenylate (2-5 A) system in mediating RNA cleavage via RNaseL (see, for example, Cole et al., 1997, J. Biol. Chem., 272, 19187-92).

In some embodiments, contemplated nucleic acids may be a nucleic acid based compound and/or composition. For example, a contemplated nucleic acid may be a multifunctional short interfering nucleic acid (multifunctional siNA) molecule that modulates the expression of one or more genes in a biologic system (cell, tissue, or organism). Multifunctional short interfering nucleic acid or multifunctional siNA molecules are also contemplated and may be potent mediators of sequence specific regulation of gene expression—(multifunctional siNA molecules represent a class of polynucleotide molecules that are designed such that each strand in the multifunctional siNA construct comprises nucleotide sequence that is complementary to a distinct nucleic acid sequence in one or more target nucleic acid molecules).

It should be appreciated that in some embodiments, a nucleic acid may be associated with (i.e., via a bond or a linker) to another chemical or biological species. For example, contemplated herein is a nucleic acid that is associated with an enzyme, nuclease, protein, peptide, another nucleic acid, molecule, or compound. For example, in some embodiments a contemplated nucleic acid is a guide RNA and the enzyme is Cas9, as in for example, CRISPR/cas9. In some embodiments, the nucleic acid could be associated with a ZNF (zinc finger nuclease) or a TALEN (transcription activator-like effector nucleases).

In some embodiments, disclosed nanoparticles may include about 0.2 to about 35 weight percent, about 0.2 to about 20 weight percent, about 0.2 to about 10 weight percent, about 0.2 to about 5 weight percent, about 0.5 to about 5 weight percent, about 0.75 to about 5 weight percent, about 1 to about 5 weight percent, about 2 to about 5 weight percent, about 3 to about 5 weight percent, about 1 to about 20 weight percent, about 2 to about 20 weight percent, about 5 to about 20 weight percent, about 1 to about 15 weight percent, about 2 to about 15 weight percent, about 3 to about 15 weight percent, about 4 to about 15 weight percent, about 5 to about 15 weight percent, about 1 to about 10 weight percent, about 2 to about 10 weight percent, about 3 to about 10 weight percent, about 4 to about 10 weight percent, about 5 to about 10 weight percent, about 10 to about 30 weight percent, or about 15 to about 25 weight percent of a nucleic acid.

In certain aspects disclosed nanoparticles comprise a hydrophobic counter ion that is effective in transcellular/transcytosis, potocytosis, endocytosis, or biosynthetic transport functions. It should be appreciated that transcytosis may include receptor-mediated transcytosis. It should also be appreciated that endocytosis may also include any type of receptor mediated endocytosis. For example, endocytosis may involve caveolae, the invaginations in plasma membranes that have the potential to undergo endocytosis. Endocytosis may also include clathrin-mediated endocytosis. In some embodiments of the disclosed nanoparticle, the hydrophobic counter ion is an endo-lysosomal disrupting agent that is able to break the membrane of the endosome.

In certain embodiments, disclosed nanoparticles comprise a hydrophobic counter ion agent, such as an endo-lysosomal disrupting agent, and/or are prepared by a process that includes a hydrophobic counter ion agent, such as an endo-lysosomal disrupting agent. Such nanoparticles may achieve efficient transfection while preserving the integrity of the nucleic acid over nanoparticles without a hydrophobic counter ion agent, such as an endo-lysosomal disrupting agent. For example, transfection of a nucleic acid without a nanoparticle may result in degradation of the nucleic acid, rendering it therapeutically useless.

In certain embodiments, disclosed nanoparticles are associated with a hydrophobic counter ion, such as an endo-lysosomal disrupting agent. For example, disclosed nanoparticles could be in a solution with a hydrophobic counter ion. In other embodiments, disclosed nanoparticles are in a pharmaceutical composition that further comprises a hydrophobic counter ion.

Figure 10A:
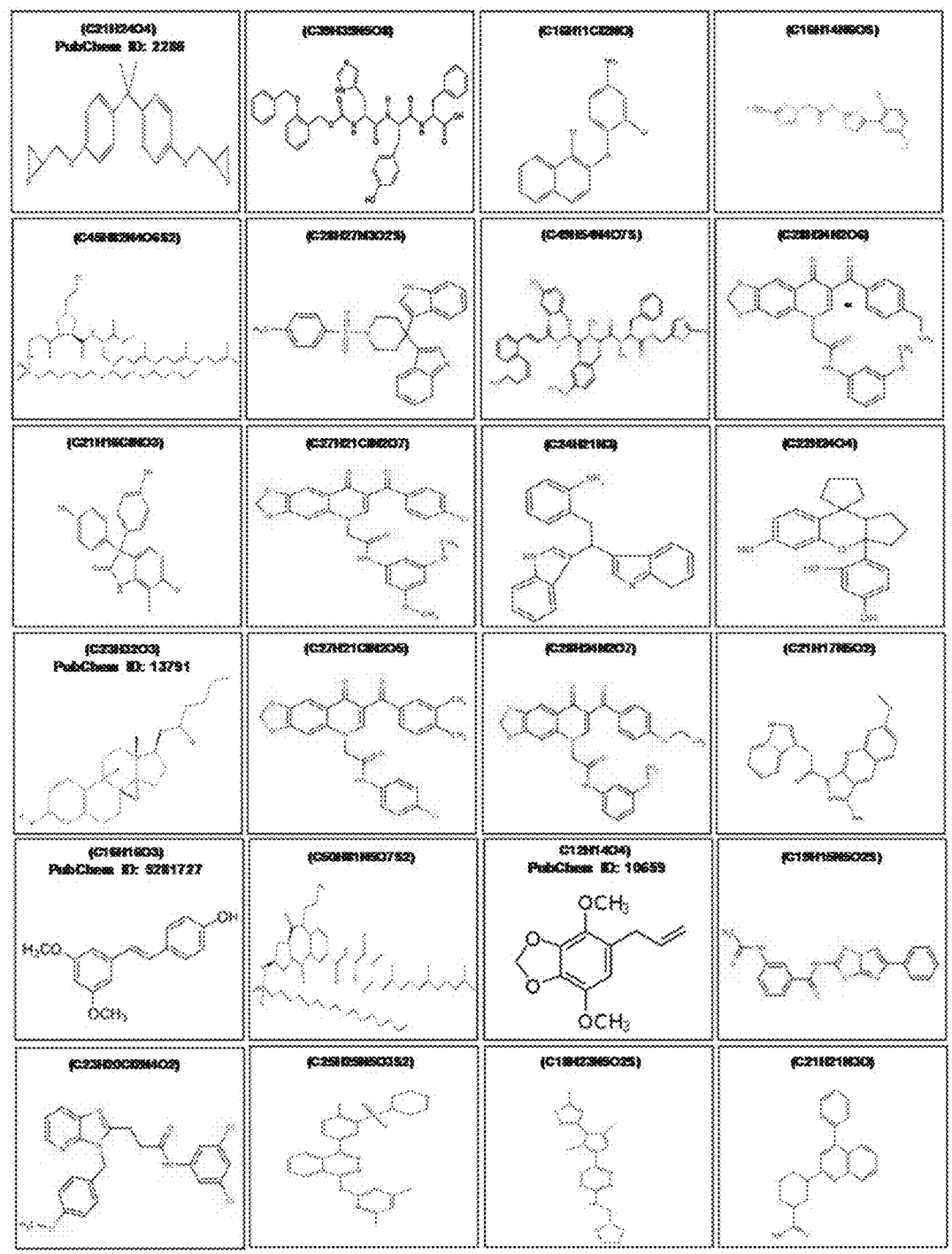
FIGS. 10A and 10B, includes contemplated hydrophobic counter ion agents, such as endo-lysosomal disrupting agents.
Figure 10B:
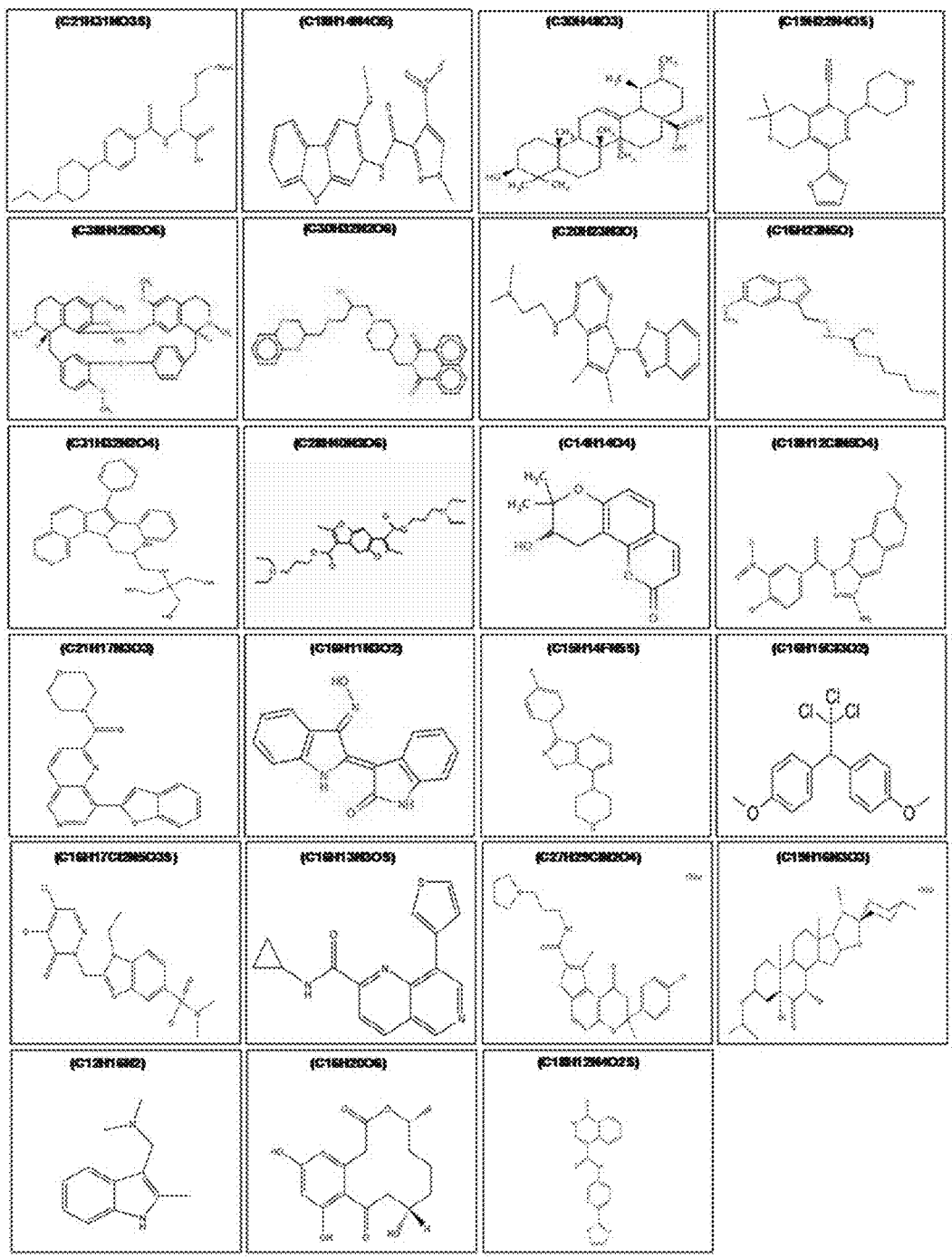

Any suitable hydrophobic counter ion agent, such as an endo-lysosomal disrupting agent, is contemplated for use in the disclosed nanoparticles. For example, an endo-lysosomal disrupting agent, may be any molecule, ion, or compound that is capable of, for example, substantially avoiding and/or limiting the processes of an endosome or lysosome of a cell. As contemplated herein, endocytosis is a pathway into the cell. In the process of endocytosis, endosomes are formed. Endo-lysosomal agents are able to break the membrane of the endosome and escape transport to a lysosome for destruction. Such agents may include compounds having mechanisms of action related to endosome or lysosome maturation, processing, and/or recycling. Exemplary hydrophobic counter ion agents, such as endo-lysosomal disrupting agents, are preferable postively charged and are able to form ion pairs with nucleic acids, and/or have a log P of greater than about 1 or greater than about 2, e.g., about 2 to about 4 or more. Exemplary hydrophobic counter ion agents (which may be an endo-lysosomal disrupting agent) include tetrandrine, notriptyline, astemizole, terfenadine, perhexaline, mepyramine, hydroxyzine, alimenazine, cyamemazine, dibucaine, propericiazine, thioproperazine, trihexyphenidyl, leelamine, ethyl lauryl arginatechl, promazine, tamoxifen, clomiphene, raloxifene, tamoxifen citrate, toremifene, clomiphene citrate, toremifene citrate, verapamil, dilitiazem, amlodipine, nifedpine, verapamil hydrochloride, nimodipine, felodipine, nicardpine, nisoldipine clevidipine, isradipine, trandolapril/verapamil, desipramine, imipramine, amitriptyline, nortiptyline, clomipramine, doxepin, amoxapine, trimipramine, protriptyline, amiodarone, lidocaine, sotalol, dronedarone, flecainide, procainamide, propafenone, quinidine, dofetilide, mexiletine, ibutilide, disopyramide, paroxetine, fluoxetine, sertraline, escitalopram, citalopram, fluvoxamine, paroxetine hydrochloride, nefazodone, citalopram hydrobromide, escitalopram oxalate, olanzapine/fluoxetine, chlorcyclizine, amodiaquine, thioridazine, chloroquine, quinine, atovaquone/proguanil, atovaquone, fluoxetine, mefloquine, primaquine, quinacrine, quinidine, halofantrine, Chloroquine, monensin, chlorcyclizine, Antrafenine, Aripiprazole, Bifeprunox, Brexpiprazole, Cariprazine, Ciprofloxacin, Dapiprazole, Dropropizine, Elopiprazole, Etoperidone, Itraconazole, Ketoconazole, Levodropropizine, Mepiprazole, Mianserin, Naftopidil, Nefazodone, Niaprazine, Oxypertine, Posaconazole, Trazodone, Umespirone, Urapidil, Vesnarinone, Lubazodone, Acaprazine, Batoprazine, Bifeprunox, Vortioxetine, Vilazodone, Tolpiprazole, Sonepiprazole, Pardoprunox, Naphthylpiperazine, Naluzotan, Lorpiprazole, Flesinoxan, Fluprazine, Flibanserin, Ensaculin, Enpiprazole, Eltoprazine, Elopiprazole, UNC 7938, sphingosine, dodecylimidazole, bafilomycin A1, quinolones, Omeprazole, Esmoprazole, pantoprazole, lansoprazole, rabeprazole, dexiansoprazole, Brefeldin A, Golgicide, Dyasore, Pitstop, amodiaquine, EGA (4-bromobenzaldehyde N-(2,6-dimethylphenyl)semicarbazone), fluoxetine, paroxetine, sertraline, thioridazine, phenothiazine, promethazine, prochlorperzaine, trifluoperazine, fluphenazine, prochlorperzine, fluphenazine decanoate, promethazine hydrochloride, quinine, Calcimycin, mefloquine, aprindine, disopyramide, flecainide, lidocaine, mexiletine, pentisomide, propafenone, cyproheptadine azatadine, ketotifen, loratadine, pizotifen, amitriptyline, propranolol, rupatadine, deptropine, amisulpride, nortriptyline, cyclobenzaprine, octriptyline, butriptyline, iprindole, trimipramine, flavoxate, cinnarizine chlomipramine, fluoxetine, promazine, imipramine, sertraline, carbamazepine, ay9944, Clomipramine, clozapine, flecainide, haloperidol, ketoconazole, ofloxacin, perhexiline, sotalol, temoxiphen, zimelidine, Cyproheptadine, toremifene, fluphenazine, trifluoperazine, pizotyline, CGS 12066B, Prochlorperazine, Doxepin, ketotifen, lacidipine, sb 205607, lofepramine, mifepristone, clobenpropit, salmeterol, azelastine, azelastine, epinastine, desloratadine, am-251, indatraline, nelfinavir, haloperidol, benproperine, M-paroxetine, carvedilol, calcipotriol, perphenazine, phenothiazine, chlorprothixene, desipramine, tetracaine, ifenprodil, U18666A, diphenhydramine among others. FIGS. 10A and 10B depict further compounds that may be hydrophobic counterion agents.

In an embodiment, the hydrophobic counter agent may be a compound represented by the following:

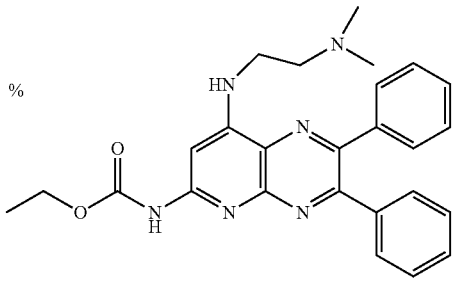 [SMILES: CCOC(=O)Nc1cc(NCCN(C)C)c2nc(-c3ccccc3)c(-c3ccccc3)nc2n1]

which may improve, for example, siRNA delivery.

The hydrophobic counter ion agent, such as an endo-lysosomal disrupting agent, may completely avoid, in some embodiments, endsome and lysosome processes, or may reduce the occurrence of endosome or lysosomal processes. As contemplated herein, the hydrophobic counter ion agent, such as an endo-lysosomal disrupting agent, forms an ion pair with a nucleic acid. The hydrophobic counter ion agent, such as an endo-lysosomal disrupting agent, reduces the occurrence of the nucleic acid—endo-lysosmal escape agent ion pair complex from endosome and/or lysosome processes. Examples of a hydrophobic counter ion agent, such as an endo-lysosomal disrupting agent, may include desipramine, amidoarone, fluoxetine chlorcyclizine, amodiaquine, paroxetine, tamoxifen, verapamil, thioridazine, chloroquine, chlorpromazine, monensin, sphingosine, dodecylimidazole, bafilomycin A1, golgicide, dyasore, Pitstop, EGA (4-bromobenzaldehyde N-(2,6-dimethylphenyl) semicarbazone), sertraline, calcimycin, mefloquine, primaquine, quinacrine, halofantrine, quinine, stearylamine, oleylamine, dioleylamine, N-methyl-N,N-dioleylamine, and N,N-dimethyloleylamine, DODAC (dioleoyldimethylammonium chloride), DDAB (Dimethyldioctadecylammonium), DMAB (Didodecyldimethylammonium bromide), DOPE (dioleoylphosphatidylethanolamine), DSDMA (1,2-distearyloxy-N,N-dimethyl-3-aminopropane), DODMA (1,2-dioleyloxy-N,N-dimethyl-3-aminopropane), 3ß-[N—(N',N'-dimethylaminoethane)-carbamoyl]cholesterol hydrochloride (DC-Cholesterol.HCl), DMRIE, LIPOFECTIN (commercially available cationic liposomes comprising DOTMA and DOPE, from GIBCO/BRL, Grand Island, N.Y., USA), LIPOFECTAMINE (commercially available cationic liposomes comprising DOSPA and DOPE, from GIBCO/BRL), TRANSFECTAM (commercially available cationic lipids comprising DOGS from Promega Corp., Madison, Wis., USA), DOTMA (1,2-di-O-octadecenyl-3-trimethylammonium propane), diallyldimethylammonium chloride, Dimethyldioctadecylammonium chloride, DOTAP (1,2-dioleoyl-3-trimethylammonium-propane (chloride salt)), DODAP (1,2-dioleoyloxy-3-dimethylamino-propane), 1-oleoyl-2-hydroxy-3-N,N-dimethylamino propane, 1,2-diacyl-3-N,N-dimethylamino propane, 1,2-didecanoyl-1-N,N-dimethylamino propane2, phosphatidylcholine, phosphatidylethanolamine, phosphatidylserine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine, Diacyl phosphatidylcholine, diacyl phosphatidylethanolamine, Sphingosine and derivatives of sphingosine having additional fatty acid chains, or alkyl groups, attached to either of the pendent hydroxyl groups and/or attached to the amino functional group, a polyamine (such as putrescine, cadaverine, spermidine, and spermine) and polyethylenimine (PEI). It should be appreciated that the hydrophobic counter ion agent may be a salt derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N.sup.1-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Bases may be Ammonia, Anion-exchange resins, e.g. cholestyramine resin, Arginine, Benethamine, Benzathine, Tert-butylmane, Choline, Deanol, Diethanolamine, Diethylamine, Epolamine, Ethylenediamine, Hydrabamine, Imidazole, Lysine, Morpholine, 4-(2-hydroxyethyl), Piperazine, Pyrrolidine, 1-(2-hydroxyethyl), Triethanolamine and tromethamine.

In some embodiments, the nucleic acid and hydrophobic counter ion agent, such as an endo-lysosomal disrupting agent, also referred to herein as a counter ion, form an ion pair. In some embodiments, the number of counter ions, or endo-lysosomal escape agents, are associated with a nucleic acid molecule to balance the charge, or to achieve a zeta potential between about 10 and about −10 mV (or e.g., about 20 mV to about −20 mV, or about 5 to −5 mV) for the ion pair. A combination of endo-lysosomal escape agents and inactive hydrophobic cations can be used to adjust the dose of EE agent if needed to effect the desired activity. For example, if a nucleic acid molecule has 20 negative charges, 20 counter ions may associate with a single nucleic acid molecule. In this example, the ratio of nucleic acid molecules to counter ions is 1:20. It should be appreciated that this ratio would depend on the number of charges on the nucleic acid molecule and the hydrophobic counter ion agent(s), such as an endo-lysosomal disrupting agent(s).

In some embodiments, the hydrophobic counter ion agent, such as an endo-lysosomal disrupting agent, may have a log P of between about 2 and about 15, in some embodiments between about 1 and about 2, in some embodiments between about 5 and about 15, in some embodiments between about 5 and about 10, in some embodiments between about 2 and about 8, in some embodiments between about 4 and about 8, in some embodiments between about 2 and about 7, or in some embodiments between about 4 and about 7. In some instances, the hydrophobic acid may have a log P greater than about 2, greater than about 4, greater than about 5, or greater than 6.

In some instances, the concentration of hydrophobic counter ion agent, such as an endo-lysosomal disrupting agent, in a solution (i.e., a nucleic acid solution) may be between about 1 weight percent and about 30 weight percent, in some embodiments between about 2 weight percent and about 30 weight percent, in some embodiments between about 3 weight percent and about 30 weight percent, in some embodiments between about 4 weight percent and about 30 weight percent, in some embodiments between about 5 weight percent and about 30 weight percent, in some embodiments between about 6 weight percent and about 30 weight percent, in some embodiments between about 8 weight percent and about 30 weight percent, in some embodiments between about 10 weight percent and about 30 weight percent, in some embodiments between about 12 weight percent and about 30 weight percent, in some embodiments between about 14 weight percent and about 30 weight percent, in some embodiments between about 16 weight percent and about 30 weight percent, in some embodiments between about 1 weight percent and about 5 weight percent, in some embodiments between about 3 weight percent and about 9 weight percent, in some embodiments between about 6 weight percent and about 12 weight percent, in some embodiments between about 9 weight percent and about 15 weight percent, in some embodiments between about 12 weight percent and about 18 weight percent, and in some embodiments between about 15 weight percent and about 21 weight percent. In certain embodiments, the concentration of counter ion in a nucleic acid solution may be at least about 1 weight percent, in some embodiments at least about 2 weight percent, in some embodiments at least about 3 weight percent, in some embodiments at least about 5 weight percent, in some embodiments at least about 10 weight percent, in some embodiments at least about 15 weight percent, and in some embodiments at least about 20 weight percent.

In certain embodiments, the molar ratio of hydrophobic counter ion agent, such as an endo-lysosomal disrupting agent, to nucleic acid (e.g., initially during formulation of the nanoparticles and/or in the nanoparticles) may be between about 0.25:1 to about 6:1, in some embodiments between about 0.25:1 to about 5:1, in some embodiments between about 0.25:1 to about 4:1, in some embodiments between about 0.25:1 to about 3:1, in some embodiments between about 0.25:1 to about 2:1, in some embodiments between about 0.25:1 to about 1.5:1, in some embodiments between about 0.25:1 to about 1:1, in some embodiments between about 0.25:1 to about 0.5:1, in some embodiments between about 0.5:1 to about 6:1, in some embodiments between about 0.5:1 to about 5:1, in some embodiments between about 0.5:1 to about 4:1, in some embodiments between about 0.5:1 to about 3:1, in some embodiments between about 0.5:1 to about 2:1, in some embodiments between about 0.5:1 to about 1.5:1, in some embodiments between about 0.5:1 to about 1:1, in some embodiments between about 0.5:1 to about 0.75:1, in some embodiments between about 0.75:1 to about 2:1, in some embodiments between about 0.75:1 to about 1.5:1, in some embodiments between about 0.75:1 to about 1.25:1, in some embodiments between about 0.9:1 to about 1.1:1, in some embodiments between about 0.95:1 to about 1.05:1, in some embodiments about 1:1, in some embodiments between about 0.75:1 to about 1:1, in some embodiments between about 1:1 to about 6:1, in some embodiments between about 1:1 to about 5:1, in some embodiments between about 1:1 to about 4:1, in some embodiments between about 1:1 to about 3:1, in some embodiments between about 1:1 to about 2:1, in some embodiments between about 1:1 to about 1.5:1, in some embodiments between about 1.5:1 to about 6:1, in some embodiments between about 1.5:1 to about 5:1, in some embodiments between about 1.5:1 to about 4:1, in some embodiments between about 1.5:1 to about 3:1, in some embodiments between about 2:1 to about 6:1, in some embodiments between about 2:1 to about 4:1, in some embodiments between about 3:1 to about 6:1, in some embodiments between about 3:1 to about 5:1, and in some embodiments between about 4:1 to about 6:1.

In some instances, the initial molar ratio of hydrophobic counter ion agent, such as an endo-lysosomal disrupting agent, to nucleic acid (i.e., during formulation of the nanoparticles) may be different from the molar ratio of hydrophobic counter ion agent, such as an endo-lysosomal disrupting agent, to nucleic acid in the nanoparticles (i.e., after removal of unencapsulated hydrophobic counter ion agent, such as an endo-lysosomal disrupting agent, and nucleic acid). In other instances, the initial molar ratio of hydrophobic counter ion agent, such as an endo-lysosomal disrupting agent, to nucleic acid (i.e., during formulation of the nanoparticles) may be essentially the same as the molar ratio hydrophobic counter ion agent, such as an endo-lysosomal disrupting agent, to nucleic acid in the nanoparticles (i.e., after removal of unencapsulated hydrophobic counter ion agent, such as an endo-lysosomal disrupting agent, and nucleic acid).

In some cases, a solution containing the nucleic acid may be prepared separately from a solution containing the polymer, and the two solutions may then be combined prior to nanoparticle formulation. For instance, in one embodiment, a first solution contains the nucleic acid and hydrophobic counter ion agent, such as an endo-lysosomal disrupting agent, and a second solution contains the polymer and optionally the hydrophobic counter ion agent, such as an endo-lysosomal disrupting agent. Formulations where the second solution does not contain the hydrophobic counter ion agent, such as an endo-lysosomal disrupting agent, may be advantageous, for example, for minimizing the amount hydrophobic counter ion agent, such as an endo-lysosomal disrupting agent, used in a process or, in some cases, for minimizing contact time between the hydrophobic counter ion agent, such as an endo-lysosomal disrupting agent, and, e.g., a polymer that can degrade in the presence of the hydrophobic counter ion agent, such as an endo-lysosomal disrupting agent. In other cases, a single solution may be prepared containing the nucleic acid, polymer, and hydrophobic counter ion agent, such as an endo-lysosomal disrupting agent.

In some embodiments, the nucleic acid—hydrophobic counter ion agent, such as an endo-lysosomal disrupting agent, ion pair may be formed prior to formulation of the nanoparticles. For example, a solution containing the ion pair may be prepared prior to formulating the contemplated nanoparticles (e.g., by preparing a solution containing suitable amounts of the nucleic acid and the hydrophobic counter ion agent, such as an endo-lysosomal disrupting agent). In other embodiments, the ion pair may be formed during formulation of the nanoparticles. For example, a first solution containing the nucleic acid and a second solution containing the hydrophobic counter ion agent, such as an endo-lysosomal disrupting agent, may be combined during a process step for preparing the nanoparticles (e.g., prior to emulsion formation and/or during emulation formation). In certain embodiments, the ion pair may form prior to encapsulation of the nucleic acid and hydrophobic counter ion agent, such as an endo-lysosomal disrupting agent, in a contemplated nanoparticle. In other embodiments, the ion pair may form in the nanoparticle, e.g., after encapsulation of the nucleic acid and hydrophobic counter ion agent, such as an endo-lysosomal disrupting agent.

In certain embodiments, the hydrophobic counter ion agent, such as an endo-lysosomal disrupting agent, may have a solubility of less than about 2 g per 100 mL of water, in some embodiments less than about 1 g per 100 mL of water, in some embodiments less than about 100 mg per 100 mL of water, in some embodiments less than about 10 mg per 100 mL of water, and in some embodiments less than about 1 mg per 100 mL of water, determined at 25° C. In other embodiments, the acid may have a solubility of between about 1 mg per 100 mL of water to about 2 g per 100 mL of water, in some embodiments between about 1 mg per 100 mL of water to about 1 g per 100 mL of water, in some embodiments between about 1 mg per 100 mL of water to about 500 mg per 100 mL of water, and in some embodiments between about 1 mg per 100 mL of water to about 100 mg per 100 mL of water, determined at 25° C. In some embodiments, the hydrophobic counter ion agent, such as an endo-lysosomal disrupting agent, may be essentially insoluble in water at 25° C.

In some embodiments, disclosed nanoparticles may be essentially free of the hydrophobic counter ion agent, such as an endo-lysosomal disrupting agent, used during the preparation of the nanoparticles. In other embodiments, disclosed nanoparticles may comprise hydrophobic counter ion agent, such as an endo-lysosomal disrupting agent. For instance, in some embodiments, the hydrophobic counter ion agent, such as an endo-lysosomal disrupting agent, content in disclosed nanoparticles may be between about 0.05 weight percent to about 35 weight percent, in some embodiments between about 0.05 weight percent to about 30 weight percent, in some embodiments between about 0.5 weight percent to about 30 weight percent, in some embodiments between about 1 weight percent to about 30 weight percent, in some embodiments between about 2 weight percent to about 30 weight percent, in some embodiments between about 3 weight percent to about 30 weight percent, in some embodiments between about 5 weight percent to about 30 weight percent, in some embodiments between about 7 weight percent to about 30 weight percent, in some embodiments between about 10 weight percent to about 30 weight percent, in some embodiments between about 15 weight percent to about 30 weight percent, in some embodiments between about 20 weight percent to about 30 weight percent, in some embodiments between about 0.05 weight percent to about 0.5 weight percent, in some embodiments between about 0.05 weight percent to about 5 weight percent, in some embodiments between about 1 weight percent to about 5 weight percent, in some embodiments between about 3 weight percent to about 10 weight percent, in some embodiments between about 5 weight percent to about 15 weight percent, and in some embodiments between about 10 weight percent to about 20 weight percent.

In some embodiments, disclosed nanoparticles substantially release (e.g., over about 1 minute to about 30 minutes, about 1 minute to about 25 minutes, about 5 minutes to about 30 minutes, about 5 minutes to about 1 hour, about 1 hour, or about 24 hours) less than about 2%, less than about 5%, less than about 10%, less than about 15%, less than about 20%, less than about 25%, less than about 30%, or less than 40% of the nucleic acid, or the nucleic acid—hydrophobic counter ion agent (such as an endo-lysosomal disrupting agent), for example, when placed in a phosphate buffer solution at room temperature (e.g., 25° C.) and/or at 37° C. In certain embodiments, nanoparticles comprising a nucleic acid may release the nucleic acid, or nucleic acid-hydrophobic counter ion(s) when placed in an aqueous solution (e.g., a phosphate buffer solution), e.g., at 25° C. and/or at 37° C., at a rate substantially corresponding to about 0.01 to about 50%, in some embodiments about 0.01 to about 25%, in some embodiments about 0.01 to about 15%, in some embodiments about 0.01 to about 10%, in some embodiments about 1 to about 40%, in some embodiments about 5 to about 40%, and in some embodiments about 10 to about 40% of the protonatable nitrogen-containing therapeutic agent released over about 1 hour. In some embodiments, nanoparticles comprising a protonatable nitrogen-containing therapeutic agent may release the protonatable nitrogen-containing therapeutic agent when placed in an aqueous solution (e.g., a phosphate buffer solution), e.g., at 25° C. and/or at 37° C., at a rate substantially corresponding to about 10 to about 70%, in some embodiments about 10 to about 45%, in some embodiments about 10 to about 35%, or in some embodiments about 10 to about 25%, of the protonatable nitrogen-containing therapeutic agent released over about 4 hours.

In some embodiments, disclosed nanoparticles may substantially retain the nucleic acid, e.g., for at least about 1 minute, at least about 1 hour, or more, when placed in a phosphate buffer solution at 37° C.

In one embodiment, disclosed therapeutic nanoparticles may include a targeting ligand, e.g., a low-molecular weight ligand. In certain embodiments, the low-molecular weight ligand is conjugated to a polymer, and the nanoparticle comprises a certain ratio of ligand-conjugated polymer (e.g., PLA-PEG-Ligand) to non-functionalized polymer (e.g., PLA-PEG or PLGA-PEG). The nanoparticle can have an optimized ratio of these two polymers such that an effective amount of ligand is associated with the nanoparticle for treatment of a disease or disorder, such as cancer. For example, an increased ligand density may increase target binding (cell binding/target uptake), making the nanoparticle "target specific." Alternatively, a certain concentration of non-functionalized polymer (e.g., non-functionalized PLGA-PEG copolymer) in the nanoparticle can control inflammation and/or immunogenicity (i.e., the ability to provoke an immune response), and allow the nanoparticle to have a circulation half-life that is adequate for the treatment of a disease or disorder. Furthermore, the non-functionalized polymer may, in some embodiments, lower the rate of clearance from the circulatory system via the reticuloendothelial system (RES). Thus, the non-functionalized polymer may provide the nanoparticle with characteristics that may allow the particle to travel through the body upon administration. In some embodiments, a non-functionalized polymer may balance an otherwise high concentration of ligands, which can otherwise accelerate clearance by the subject, resulting in less delivery to the target cells.

In some embodiments, nanoparticles disclosed herein may include functionalized polymers conjugated to a ligand that constitute approximately 0.1-50, e.g., 0.1-30, e.g., 0.1-20, e.g., 0.1-10 mole percent of the entire polymer composition of the nanoparticle (i.e., functionalized+non-functionalized polymer). Also disclosed herein, in another embodiment, are nanoparticles that include a polymer conjugated (e.g., covalently with (e.g., through a linker (e.g., an alkylene linker)) or a bond) with one or more low-molecular weight ligands, wherein the weight percent low-molecular weight ligand with respect to total polymer is between about 0.001 and 5, e.g., between about 0.001 and 2, e.g., between about 0.001 and 1.

In some embodiments, disclosed nanoparticles may be able to bind efficiently to or otherwise associate with a biological entity, for example, a particular membrane component or cell surface receptor. It should be appreciated that peptides, ligands, proteins, antibodies, or nanobodies can also be used to target the nanoparticles. Targeting of a therapeutic agent, or a nucleic acid, (e.g., to a particular tissue or cell type, to a specific diseased tissue but not to normal tissue, etc.) is desirable for the treatment of tissue specific diseases such as solid tumor cancers (e.g., prostate cancer). For example, in contrast to systemic delivery of a cytotoxic anticancer agent, the nanoparticles disclosed herein may substantially prevent the agent from killing healthy cells. Additionally, disclosed nanoparticles may allow for the administration of a lower dose of the agent (as compared to an effective amount of agent administered without disclosed nanoparticles or formulations) which may reduce the undesirable side effects commonly associated with traditional chemotherapy.

In general, a "nanoparticle" refers to any particle having a diameter of less than 1000 nm, e.g., about 10 nm to about 200 nm. Disclosed therapeutic nanoparticles may include nanoparticles having a diameter of about 60 to about 120 nm, or about 70 to about 120 nm, or about 80 to about 120 nm, or about 90 to about 120 nm, or about 100 to about 120 nm, or about 60 to about 130 nm, or about 70 to about 130 nm, or about 80 to about 130 nm, or about 90 to about 130 nm, or about 100 to about 130 nm, or about 110 to about 130 nm, or about 60 to about 140 nm, or about 70 to about 140 nm, or about 80 to about 140 nm, or about 90 to about 140 nm, or about 100 to about 140 nm, or about 110 to about 140 nm, or about 60 to about 150 nm, or about 70 to about 150 nm, or about 80 to about 150 nm, or about 90 to about 150 nm, or about 100 to about 150 nm, or about 110 to about 150 nm, or about 120 to about 150 nm. It should be appreciated that disclosed nanoparticles may be formed at a particular size, which may determine uptake pathways, circulation time, targeting, internalization, and/or clearance.

Polymers

In some embodiments, the nanoparticles may comprise a matrix of polymers and a therapeutic agent, such as a nucleic acid as described above, optionally together with a hydrophobic counter ion agent, such as an endo-lysosomal disrupting agent. In some embodiments, a therapeutic agent and/or targeting moiety (e.g., a low-molecular weight ligand) can be associated with at least part of the polymeric matrix. For example, in some embodiments, a targeting moiety (e.g., ligand) can be covalently associated with the surface of a polymeric matrix. In some embodiments, covalent association is mediated by a linker. The therapeutic agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g., targeting moiety); and the second macromolecule comprising a second polymer that is not bound to a targeting moiety. The nanoparticle can optionally include one or more additional, unfunctionalized, polymers.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, e.g., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments include polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid (PLA)), poly(lactic) acid-co-poly(glycolic) acid (PLGA), polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

For instance, a contemplated polymer may be one that hydrolyzes spontaneously upon exposure to water (e.g., within a subject), or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight (or e.g., the ratio of molecular weights of, e.g., different blocks of a copolymer) of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer (or e.g., the ratio of molecular weights of, e.g., different blocks of a copolymer) can be adjusted such that the particle biodegrades in the subject being treated within a reasonable period of time (ranging from a few hours to 1-2 weeks, 3-4 weeks, 5-6 weeks, 7-8 weeks, etc.).

A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes about 10 to about 99 weight percent poly(lactic) acid-poly(ethylene)glycol copolymer or poly(lactic)-co-poly (glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 10 to about 20 kDa, about 15 to about 20 kDa, or about 10 to about 25 kDa of poly(lactic) acid and a number average molecular weight of about 4 to about 6, or about 2 kDa to about 10 kDa of poly(ethylene)glycol.

In some embodiments, the poly(lactic) acid-poly(ethylene)glycol copolymer may have a poly(lactic) acid number average molecular weight fraction of about 0.6 to about 0.95, in some embodiments between about 0.7 to about 0.9, in some embodiments between about 0.6 to about 0.8, in some embodiments between about 0.7 to about 0.8, in some embodiments between about 0.75 to about 0.85, in some embodiments between about 0.8 to about 0.9, and in some embodiments between about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly(ethylene)glycol component.

Disclosed nanoparticles may optionally include about 1 to about 50 weight percent poly(lactic) acid or poly(lactic) acid-co-poly (glycolic) acid (which does not include PEG), or may optionally include about 1 to about 50 weight percent, or about 10 to about 50 weight percent or about 30 to about 50 weight percent poly(lactic) acid or poly(lactic) acid-co-poly (glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

A therapeutic nanoparticle may, in some embodiments, contain about 10 to about 30 weight percent, in some embodiments about 10 to about 25 weight percent, in some embodiments about 10 to about 20 weight percent, in some embodiments about 10 to about 15 weight percent, in some embodiments about 15 to about 20 weight percent, in some embodiments about 15 to about 25 weight percent, in some embodiments about 20 to about 25 weight percent, in some embodiments about 20 to about 30 weight percent, or in some embodiments about 25 to about 30 weight percent of poly(ethylene)glycol, where the poly(ethylene)glycol may be present as a poly(lactic) acid-poly(ethylene)glycol copolymer, poly(lactic)-co-poly (glycolic) acid-poly(ethylene)glycol copolymer, or poly(ethylene)glycol homopolymer. In certain embodiments, the polymers of the nanoparticles can be conjugated to a lipid. The polymer can be, for example, a lipid-terminated PEG.

Targeting Moieties

Provided herein, in some embodiments, are nanoparticles that may include an optional targeting moiety, i.e., a moiety able to bind to or otherwise associate with a biological entity, for example, a membrane component, a cell surface receptor, an antigen, or the like. A targeting moiety present on the surface of the particle may allow the particle to become localized at a particular targeting site, for instance, a tumor, a disease site, a tissue, an organ, a type of cell, etc. As such, the nanoparticle may then be "target specific." The drug or other payload may then, in some cases, be released from the particle and allowed to interact locally with the particular targeting site.

Disclosed nanoparticles may comprise a hydroprobic ion pair that is effective in transcellular/transcytosis, potocytosis, endocytosis, or biosynthetic transport functions. In some embodiments, a targeting moiety may target a nanoparticle to a receptor site for transcytosis or endocytosis. For example, a targeting moiety can target a nanoparticle to a caveolae, which is capable of endocystosis, via the protein caveolin. In other embodiments, clathrin-coated pits and vesicles, which are known efficient pathways for taking up macromolecules, are targeted. In this process, called receptor-mediated endocytosis, the macromolecules bind to complementary transmembrane receptor proteins, accumulate in coated pits, and then enter the cell as receptor-macromolecule complexes in clathrin-coated vesicles. More than 25 different receptors are known to participate in receptor-mediated endocytosis of different types of molecules, and may use the same clathrin-coated-pit pathway (e.g., LDL receptor, transferrin receptor, receptor that binds EGF (epidermal growth factor)). Thus, it should be appreciated that contemplated targeting moieties may target different receptors that are known to participate in receptor-mediated endocytosis.

It should be appreciated that the receptor-ligand bond can dissociate and can follow pathways from the endosomal compartment. For example, inclusion of an endo-lysososmal escape agent can release the nucleic acid-hydrophobic counter ion complex into different plasma membrane domains.

In one embodiment, a disclosed nanoparticle includes a targeting moiety that is a low-molecular weight ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

For example, a targeting portion may cause the particles to become localized to a tumor (e.g., a solid tumor), a disease site, a tissue, an organ, a type of cell, etc. within the body of a subject, depending on the targeting moiety used. For example, a low-molecular weight ligand may become localized to a solid tumor, e.g., breast or prostate tumors or cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

Contemplated targeting moieties may include small molecules. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol, for example about 100 g/mol to about 600 g/mol, or about 200 g/mol to about 500 g/mol.

In some embodiments, the low-molecular weight ligand is of the Formulae I, II, III or IV:

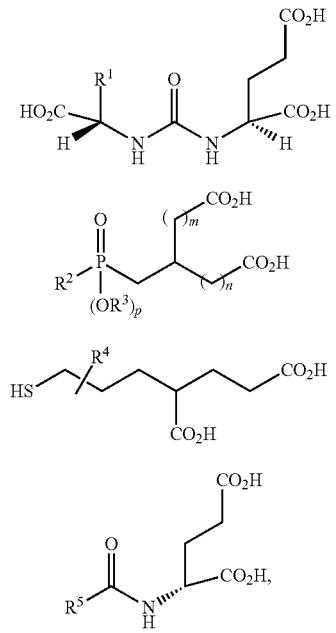

and enantiomers, stereoisomers, rotamers, tautomers, diastereomers, or racemates thereof;
wherein m and n are each, independently, 0, 1, 2 or 3; p is 0 or 1;
$R^1$, $R^2$, $R^4$, and $R^5$ are each, independently, selected from the group consisting of substituted or unsubstituted alkyl (e.g., $C_{1-10}$-alkyl, $C_{1-6}$-alkyl, or $C_{1-4}$-alkyl), substituted or unsubstituted aryl (e.g., phenyl or pyridinyl), and any combination thereof; and $R^3$ is H or $C_{1-6}$-alkyl (e.g., $CH_3$).

For compounds of Formulae I, II, III and IV, $R^1$, $R^2$, $R^4$ or $R^5$ comprise points of attachment to the nanoparticle, e.g., a point of attachment to a polymer that forms part of a disclosed nanoparticle, e.g., PEG. The point of attachment may be formed by a covalent bond, ionic bond, hydrogen bond, a bond formed by adsorption including chemical adsorption and physical adsorption, a bond formed from van der Waals bonds, or dispersion forces. For example, if $R^1$, $R^2$, $R^4$, or $R^5$ are defined as an aniline or $C_{1-6}$-alkyl-$NH_2$ group, any hydrogen (e.g., an amino hydrogen) of these functional groups could be removed such that the low-molecular weight ligand is covalently bound to the polymeric matrix (e.g., the PEG-block of the polymeric matrix) of the nanoparticle. As used herein, the term "covalent bond" refers to a bond between two atoms formed by sharing at least one pair of electrons.

In particular embodiments of the Formulae I, II, III or IV, $R^1$, $R^2$, $R^4$, and $R^5$ are each, independently, $C_{1-6}$-alkyl or phenyl, or any combination of $C_{1-6}$-alkyl or phenyl, which are independently substituted one or more times with OH, SH, $NH_2$, or $CO_2H$, and wherein the alkyl group may be interrupted by N(H), S, or O. In another embodiment, $R^1$, $R^2$, $R^4$, and $R^5$ are each, independently, $CH_2$-Ph, $(CH_2)_2$—SH, $CH_2$—SH, $(CH_2)_2C(H)(NH_2)CO_2H$, $CH_2C(H)(NH_2)CO_2H$, $CH(NH_2)CH_2CO_2H$, $(CH_2)_2C(H)(SH)CO_2H$, $CH_2$—N(H)-Ph, O—$CH_2$-Ph, or O—$(CH_2)_2$-Ph, wherein each Ph may be independently substituted one or more times with OH, $NH_2$, $CO_2H$, or SH. For these formulae, the $NH_2$, OH or SH groups serve as the point of covalent attachment to the nanoparticle (e.g., —N(H)—PEG, —O-PEG, or —S-PEG).

Exemplary ligands include:

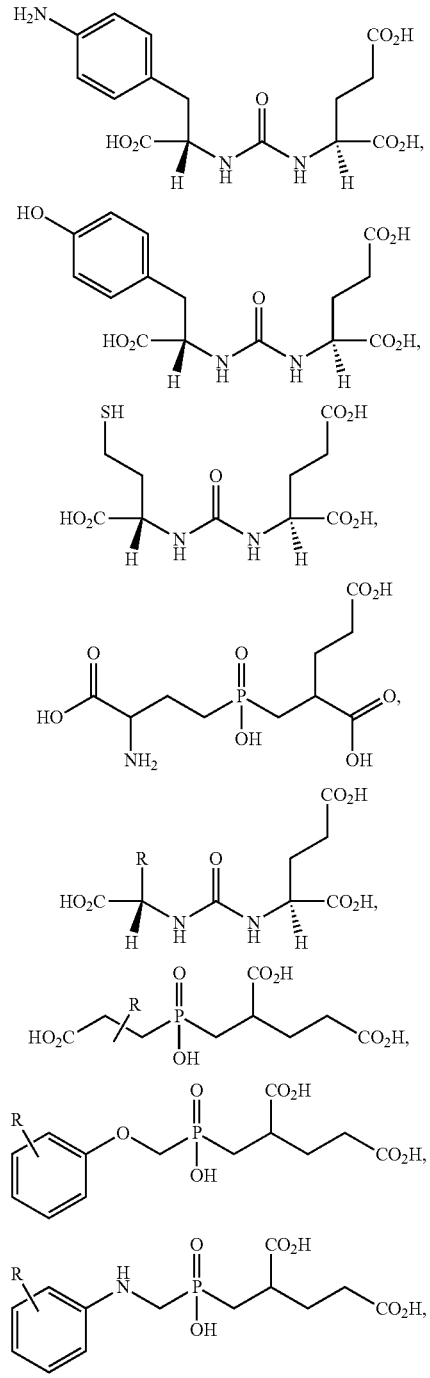

-continued

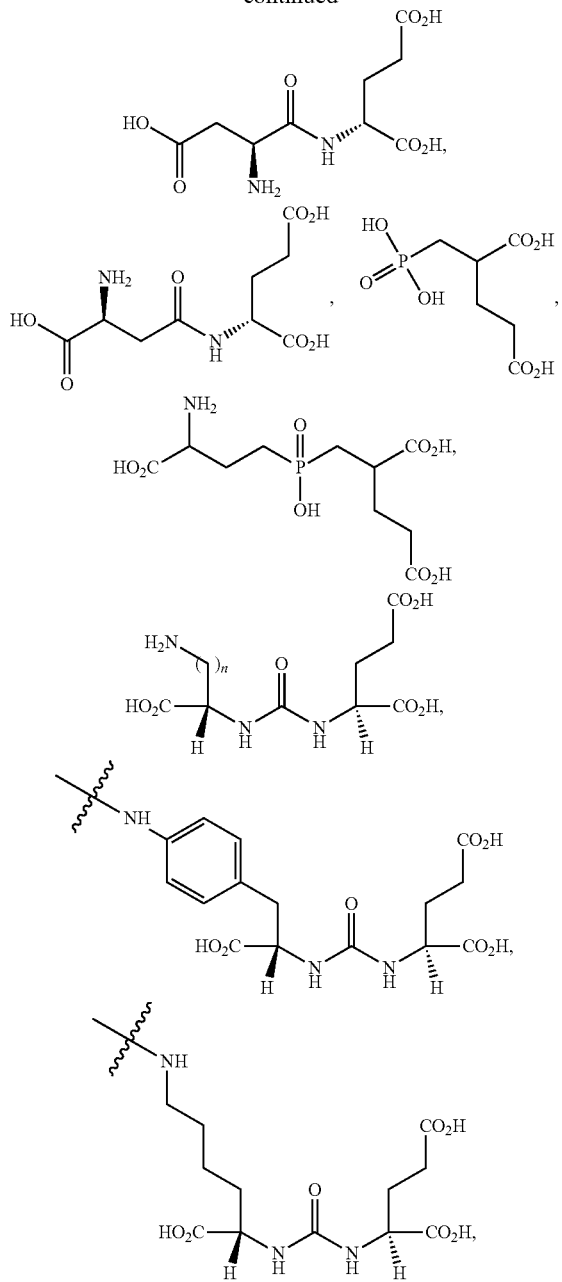

and enantiomers, stereoisomers, rotamers, tautomers, diastereomers, or racemates thereof, wherein the $NH_2$, OH, or SH groups serve as the point of covalent attachment to the nanoparticle (e.g., —N(H)—PEG, —O-PEG, or —S-PEG) or indicates the point of attachment to the nanoparticle, wherein n is 1, 2, 3, 4, 5, or 6, and wherein R is independently selected from the group consisting of $NH_2$, SH, OH, $CO_2H$, $C_1$-$C_6$-alkyl that is substituted with $NH_2$, SH, OH, or $CO_2H$, and phenyl that is substituted with $NH_2$, SH, OH, or $CO_2H$, and wherein R serves as the point of covalent attachment to the nanoparticle (e.g., —N(H)—PEG, —S-PEG, —O-PEG, or $CO_2$-PEG). These compounds may be further substituted with $NH_2$, SH, OH, $CO_2H$, $C_1$-$C_6$-alkyl that is substituted with $NH_2$, SH, OH, or $CO_2H$, or phenyl that is substituted with $NH_2$, SH, OH or $CO_2H$, wherein these functional groups can also serve as the point of covalent attachment to the nanoparticle.

In some embodiments, small molecule targeting moieties that may be used to target cells associated with solid tumors such as prostate or breast cancer tumors include PSMA peptidase inhibitors such as 2-PMPA, GPI5232, VA-033, phenylalkylphosphonamidates and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives. In some embodiments, small molecule targeting moieties that may be used to target cells associated with prostate cancer tumors include hydroxamate derivatives. In some embodiments, small molecule targeting moieties that may be used to target cells associated with prostate cancer tumors include PBDA- and urea-based inhibitors, such as ZJ 43, ZJ 11, ZJ 17, ZJ 38 and/or and analogs and derivatives thereof, androgen receptor targeting agents (ARTAs), polyamines, such as putrescine, spermine, and spermidine, inhibitors of the enzyme glutamate carboxylase II (GCPII), also known as NAAG Peptidase or NAALADase.

In some embodiments, a contemplated ligand may be a small molecule DPPIV inhibitor that may target fibroblast activation proteins (FAP) for the treatment of solid tumors. Sulfonamides (Acetozolamide and others) ligands may target G250 antigens for the treatment of ccRCC (clear cell renal cell carcinoma) and other solid tumors. A ligand may comprises chlorotoxin that may target chlorotoxin receptors for the treatment of glioblastomas and solid tumors. Small molecules may target CXCR4 and matrix metalloproteinase (MMP) for the treatment of leukemia, lymphoma, and upregulation in angiogenesis.

In another embodiment, the targeting moiety can be a ligand that targets, folate receptor or toll receptors. In another embodiment, the targeting moiety is folate, folic acid, small molecules, antibodies, and nanobodies.

Targeting moieties can include a targeting antibody. Antibodies that target EpCAM (CD326), IGF-R, Mesothelin, Lewis-Y antigen (CD174), CanAg (MUC1, PEM, CA242, CD205), NCAM (CD56), Cripto, Melanotransferrin (P97), Glycoprotein NMB (CG56972), CD70 (CD27 Ligand), 5T4 (trophoblast glycoprotein), CD57, CD44, Carcinoembryonic antigen (CEA), GD2, CD40, Fibronectin ED-B, Endoglin (CD105), Tenascin C, Phosphatidylserine (PS), HER3, CD30, CD33, CD40, CD52, CD74, CD138, CS1 (CD319, CRACC), TAG-72, CD2, CD64, ROBO4, DLL4, Tie2, and/or B7-H3 are contemplated. For example, Tenascin C may be targeted with a Tenascin C targeting antibody to treat gilomas and carcinomas. HER3 may be targeted with Heregulin or HER3 targeting antibodies to treat solid tumors. CD33 antibodies may target CD33 for treating AML. For example, antibodies targeting EpCAM (CD326), IGF-R, Mesothelin, Lewis-Y antigen (CD174), CanAg (MUC1, PEM, CA242, CD205), NCAM (CD56), and Cripto may be used for the treatment of solid tumors. Antibodies targeting Melanotransferrin (P97) may be used for treating primary and metastatic melanoma. CD30 may be targeted with antibodies for the treatment of Hodgkins and ALC lymphoma. CD74 may be targeted with antibodies for the treatment of multiple myeloma, NHL, or CLL. Affymax peptides may target TRAIL R2 for the treatment of solid tumors. Peptides such as Dyax Litt may target c-Met for the treating solid tumors. Other peptides and small molecule ligands may target EphA2 and EphB2 for the treatment of solid tumors.

For example, contemplated targeting moieties may include a nucleic acid, an aptamer, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments. Characteristic portions of antibodies, single chain targeting moieties can be identified, e.g., using procedures such as phage display.

Targeting moieties may be a targeting peptide or targeting peptidomimetic that has a length of up to about 50 residues. For example, a targeting moiety may include the amino acid sequence AKERC (SEQ ID NO: 2), CREKA (SEQ ID NO: 3), ARYLQKLN (SEQ ID NO: 4), or AXYLZZLN (SEQ ID NO: 5), wherein X and Z are variable amino acids, or conservative variants or peptidomimetics thereof. In particular embodiments, the targeting moiety is a peptide that includes the amino acid sequence AKERC (SEQ ID NO: 2), CREKA (SEQ ID NO: 3), ARYLQKLN (SEQ ID NO: 4), or AXYLZZLN (SEQ ID NO: 5), wherein X and Z are variable amino acids, and has a length of less than 20, 50 or 100 residues. The CREKA (Cys Arg Glu Lys Ala) (SEQ ID NO: 3) peptide or a peptidomimetic thereof or the octapeptide AXYLZZLN (SEQ ID NO: 5) are also contemplated as targeting moieties, as well as peptides, or conservative variants or peptidomimetics thereof, that bind or form a complex with collagen IV, or that target tissue basement membrane (e.g., the basement membrane of a blood vessel). Exemplary targeting moieties include peptides that target ICAM (intercellular adhesion molecule, e.g., ICAM-1). Other peptide based targeting moieties may be Affymax, Dyax Litt, YSA/SWL, NGR peptides and analogs with bestatin, Octreotide, CCK and Gastrin analogs, Leuprolide and analogs, GLP1/Exenatide, Lectin, and Mercator. It should be appreciated that the targeting ligands may target TRAIL R2, c-Met, EphA2, EphB2, Aminopeptidase N (CD13), VLA-4 (α4β1 integrin), CXCR4, Melanocortin receptor (MC1R), Somatostatin receptor, Cholecystokinin Receptor, GnRH Receptor, GLP1-receptor, E-Selectin, IL-11 receptor, Thrombospondin-1 receptor, Endostatin, CD79, and CD74.

Targeting moieties disclosed herein can be, in some embodiments, conjugated to a disclosed polymer or copolymer (e.g., PLA-PEG), and such a polymer conjugate may form part of a disclosed nanoparticle.

In some embodiments, a therapeutic nanoparticle may include a polymer-drug conjugate. For example, a drug may be conjugated to a disclosed polymer or copolymer (e.g., PLA-PEG), and such a polymer-drug conjugate may form part of a disclosed nanoparticle. For example, a disclosed therapeutic nanoparticle may optionally include about 0.2 to about 30 weight percent of a PLA-PEG or PLGA-PEG, wherein the PEG is functionalized with a drug (e.g., PLA-PEG-Drug).

A disclosed polymeric conjugate (e.g., a polymer-ligand conjugate) may be formed using any suitable conjugation technique. For instance, two compounds such as a targeting moiety or drug and a biocompatible polymer (e.g., a biocompatible polymer and a poly(ethylene glycol)) may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of a targeting moiety or drug and a polymer to form a polymer-targeting moiety conjugate or a polymer-drug conjugate can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety or drug) comprising an amine. For instance, a targeting moiety, such as a low-molecular weight ligand, or a drug, such as dasatinib, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. In some embodiments, a drug may be reacted with an amine-containing linker to form an amine-containing drug, which can then be conjugated to the carboxylic acid of the polymer as described above. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethylsulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol. In certain embodiments, a conjugate may be formed between an alcohol-containing moiety and carboxylic acid functional group of a polymer, which can be achieved similarly as described above for conjugates of amines and carboxylic acids.

It should be appreciated that in some embodiments, a nanoparticle may comprise two different type ligands. For example, a nanoparticle may comprise a small molecule ligand and a nucleic acid type ligand. In some embodiments, a nanoparticle may comprise three different type ligands. In some embodiments, a nanoparticle may comprise a multitude of different type ligands. It should be appreciated that a disclosed nanoparticle may include any number of different ligands.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, one polymer (e.g., copolymer, e.g., block copolymer) may include a low-molecular weight ligand, while another polymer (e.g., copolymer, e.g., block copolymer) may be chosen for its biocompatibility and/or its ability to control immunogenicity of the resultant particle.

In some embodiments, a solvent used in a nanoparticle preparation process (e.g., a nanoprecipitation process or a nanoemulsion process as discussed below) may include a hydrophobic counter ion agent, such as an endo-lysosomal disrupting agent, which may confer advantageous properties to the nanoparticles prepared using the process. As discussed above, in some cases, the hydrophobic counter ion agent, such as an endo-lysosomal disrupting agent, may improve drug loading, preserve nucleic acid integrity, and effectuate transfection of disclosed nanoparticles. Furthermore, in some instances, the controlled release properties of disclosed nanoparticles may be improved by the use of the hydrophobic counter ion agent, such as an endo-lysosomal disrupting agent. In some cases, the hydrophobic counter ion agent, such as an endo-lysosomal disrupting agent, may be included in, for example, an organic solution or an aqueous solution used in the process. In one embodiment, the drug is combined with an organic solution and the hydrophobic counter ion agent, such as an endo-lysosomal disrupting agent, and optionally one or more polymers. The hydrophobic counter ion, such as an endo-lysosomal disrupting agent, concentration in a solution used to dissolve the drug is discussed above and may be, for example, between about 1 weight percent and about 30 weight percent, etc.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Properties such as surface functionality, surface charge, size, zeta (ζ) potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties (e.g., low-molecular weight ligands) present on the surface of the particle. This allows particles having one or more specific properties to be prepared, for example, a specific size and a specific surface density of moieties, without an undue degree of effort. Accordingly, certain embodiments are directed to screening techniques using such libraries, as well as any particles identified using such libraries. In addition, identification may occur by any suitable method. For instance, the identification may be direct or indirect, or proceed quantitatively or qualitatively.

In some embodiments, already-formed nanoparticles are functionalized with a targeting moiety using procedures analogous to those described for producing ligand-functionalized polymeric conjugates. For example, a first copolymer (PLGA-PEG, poly(lactide-co-glycolide) and poly(ethylene glycol)) is mixed with the nucleic acid to form particles. The particles are then associated with a low-molecular weight ligand to form nanoparticles that can be used for the treatment of cancer, or other disorders. The particles can be associated with varying amounts of low-molecular weight ligands in order to control the ligand surface density of the nanoparticle, thereby altering the therapeutic characteristics of the nanoparticle. Furthermore, for example, by controlling parameters such as molecular weight, the molecular weight of PEG, and the nanoparticle surface charge, very precisely controlled particles may be obtained.

Figure 2A:
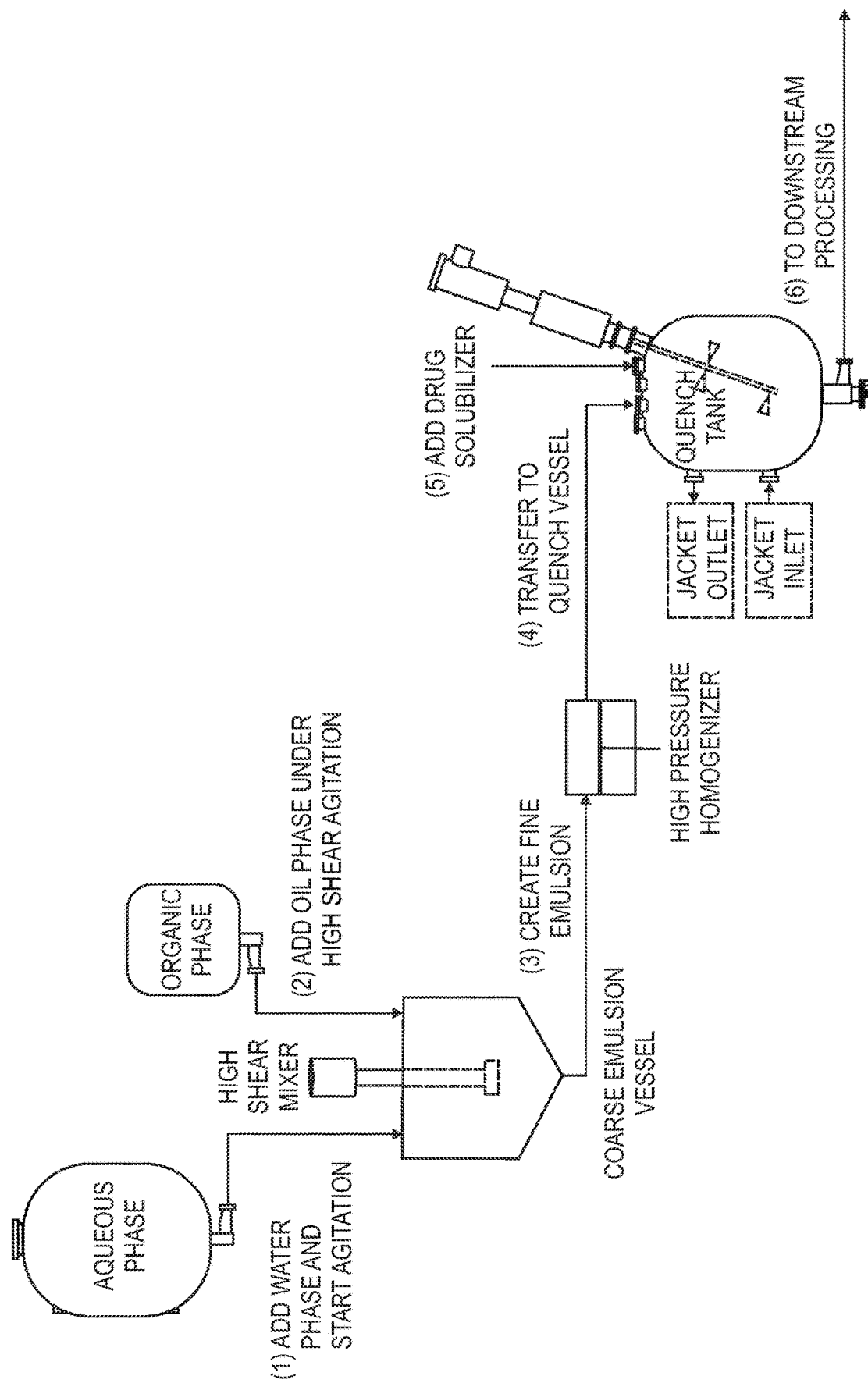
FIGS. 2A and 2B show flow diagrams for a disclosed emulsion process.
Figure 2B:
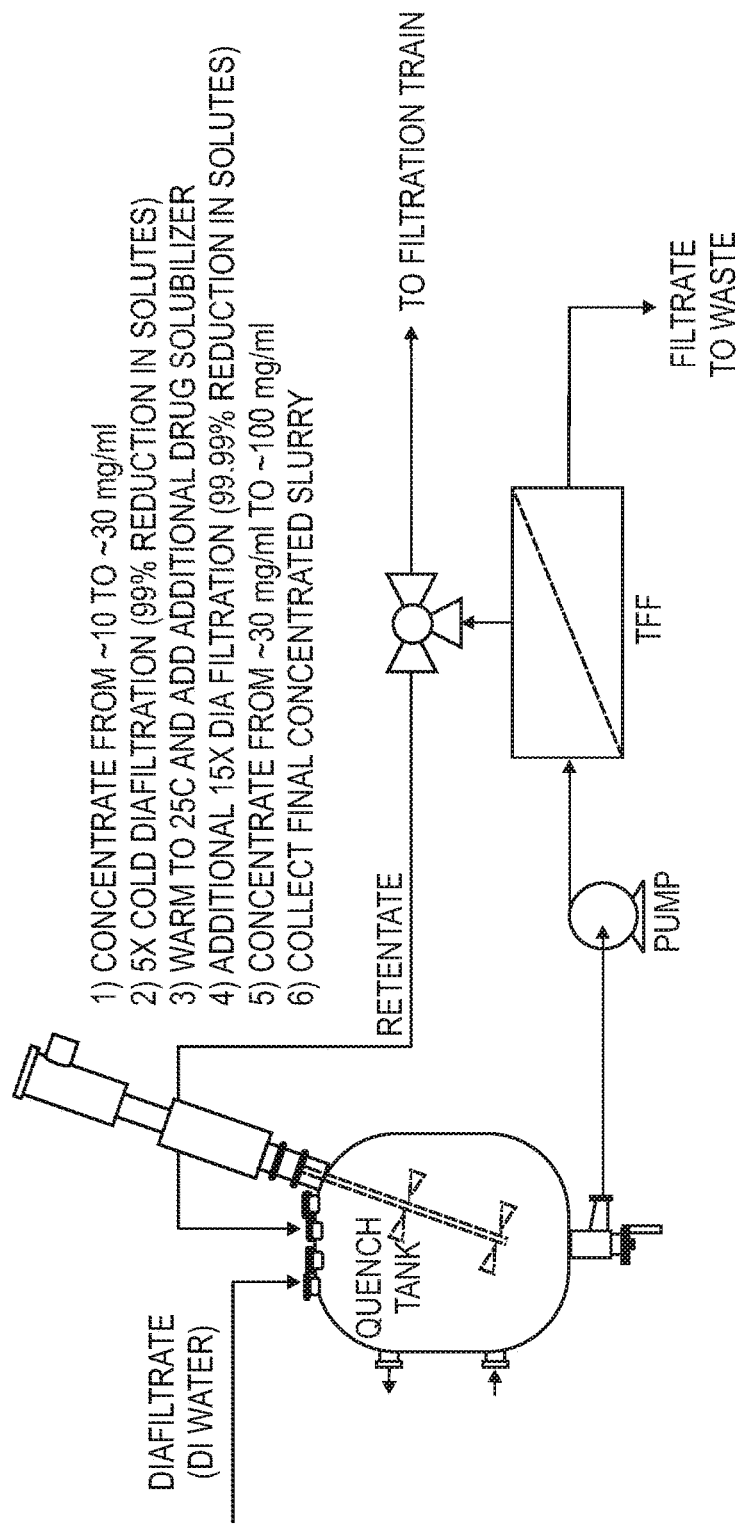

In another embodiment, a nanoemulsion process is provided, such as the process represented in FIGS. 1, 2A, and/or 2B. For example, a nucleic acid, a hydrophobic counter ion agent, such as an endo-lysosomal disrupting agent, a first polymer (for example, a diblock co-polymer such as PLA-PEG or PLGA-PEG, either of which may be optionally bound to a ligand) and an optional second polymer (e.g., (PL(G)A-PEG or PLA), may be combined with an organic solution to form a first organic phase. In other processes, the nucleic acid, and/or a hydrophobic counter ion agent is added to the aqueous phase. Such first phase may include about 1 to about 50% weight solids, about 5 to about 50% weight solids, about 5 to about 40% weight solids, about 1 to about 15% weight solids, or about 10 to about 30% weight solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. The second phase can be between about 0.1 and 50 weight %, between about 1 and 50 weight %, between about 5 and 40 weight %, or between about 1 and 15 weight %, solids. The aqueous solution can be water, optionally in combination with one or more of sodium cholate, ethyl acetate, polyvinyl acetate and benzyl alcohol. In some processes, the nucleic acid, and/or a hydrophobic counter ion agent is added to the aqueous phase. In some embodiments, the pH of the aqueous phase may be selected based on the $pK_a$ of the nucleic acid and/or the $pK_a$ of the hydrophobic counter ion agent, such as an endo-lysosomal disrupting agent. For example, in certain embodiments, the nucleic acid, may have a first $pK_a$, the hydrophobic counter ion agent, such as an endo-lysosomal disrupting agent, may have a second $pK_a$, and the aqueous phase may have a pH equal to a $pK_a$ unit between the first $pK_a$ and the second $pK_a$. In a particular embodiment, the pH of the aqueous phase may be equal to a $pK_a$ unit that is about equidistant between the first $pK_a$ and the second $pK_a$.

For example, the oil or organic phase may use a solvent that is only partially miscible with the nonsolvent (water). Therefore, when mixed at a low enough ratio and/or when using water pre-saturated with the organic solvents, the oil phase remains liquid. The oil phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate and pre-saturated with ethyl acetate and benzyl alcohol. In some instances, the organic phase (e.g., first organic phase) may include the nucleic acid. Additionally, in certain embodiments, the aqueous solution (e.g., first aqueous solution) may include the substantially hydrophobic counter ion agent, such as an endo-lysosomal disrupting agent. In other embodiments, both the nucleic acid and the substantially hydrophobic counter ion agent, such as an endo-lysosomal disrupting agent, may be dissolved in the organic phase. In other embodiments, both the nucleic acid and the substantially hydrophobic counter ion agent, such as an endo-lysosomal disrupting agent, may be dissolved in the aqueous phase.

Emulsifying the second phase to form an emulsion phase may be performed, for example, in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3, or more passes through a homogenizer. For example, when a high pressure homogenizer is used, the pressure used may be about 30 to about 60 psi, about 40 to about 50 psi, about 1000 to about 8000 psi, about 2000 to about 4000 psi, about 4000 to about 8000 psi, or about 4000 to about 5000 psi, e.g., about 2000, 2500, 4000 or 5000 psi.

In some cases, fine emulsion conditions, which can be characterized by a very high surface to volume ratio of the droplets in the emulsion, can be chosen to maximize the solubility of the nucleic acid agent and hydrophobic counter ion agent, such as an endo-lysosomal disrupting agent. In certain embodiments, under fine emulsion conditions, equilibration of dissolved components can occur very quickly, i.e., faster than solidification of the nanoparticles. Thus, selecting a hydrophobic counter ion agent, such as an endo-lysosomal disrupting agent based on, e.g., the $pK_a$ difference between the nucleic acid agent and the hydrophobic counter ion agent, such as an endo-lysosomal disrupting agent, or adjusting other parameters such as the pH of the fine emulsion and/or the pH of the quench solution, can have a significant impact on the drug loading and release properties of the nanoparticles by dictating, for example, the formation of a nucleic acid-hydrophobic counter ion(s) complex in the nanoparticle as opposed to diffusion of the nucleic acid agent and/or hydrophobic counter ion agent, such as an endo-lysosomal disrupting agent, out of the nanoparticle.

In some embodiments, the nucleic acid and the substantially hydrophobic counter ion agent, such as an endo-lysosomal disrupting agent, may be combined in the second phase prior to emulsifying the second phase. In some instances, the nucleic acid and the substantially hydrophobic counter ion agent, such as an endo-lysosomal disrupting agent, may form a nucleic acid-hydrophobic counter ion(s) complex prior to emulsifying the second phase. In other embodiments, the nucleic acid and the substantially hydrophobic counter ion agent, such as an endo-lysosomal disrupting agent, may form a nucleic acid-hydrophobic counter ion(s) complex during emulsification of the second phase. For example, the nucleic acid agent and the substantially hydrophobic counter ion agent, such as an endo-lysosomal disrupting agent, may be combined in the second phase substantially concurrently with emulsifying the second phase, e.g., the nucleic acid agent and the substantially hydrophobic counter ion agent, such as an endo-lysosomal disrupting agent, may be dissolved in separate solutions (e.g., two substantially immiscible solutions), which are then combined during emulsification. In another example, the nucleic acid and the substantially hydrophobic counter ion agent, such as an endo-lysosomal disrupting agent, may be dissolved in separate miscible solutions that are then fed into second phase during emulsification.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. In some embodiments, quenching may be performed at least partially at a temperature of about 5° C. or less. For example, water used in the quenching may be at a temperature that is less that room temperature (e.g., about 0 to about 10° C., or about 0 to about 5° C.). In certain embodiments, the quench may be chosen having a pH that is advantageous for quenching the emulsion phase, e.g., by improving the properties of the nanoparticles, such as the release profile, or improving a nanoparticle parameter, such as the drug loading. The pH of the quench may be adjusted by acid or base titration, for example, or by appropriate selection of a buffer. In some embodiments, the pH of the quench may be selected based on the $pK_a$ of the nucleic acid and/or the $pK_a$ of the hydrophobic counter ion agent, such as an endo-lysosomal disrupting agent. For example, in certain embodiments, the nucleic acid, may have a first $pK_a$, and hydrophobic counter ion agent, such as an endo-lysosomal disrupting agent, may have a second $pK_a$, and the emulsion phase may be quenched with an aqueous solution having a pH equal to a $pK_a$ unit between the first $pK_a$ and the second $pK_a$. In some embodiments, the resultant quenched phase may also have a pH equal to a $pK_a$ unit between the first $pK_a$ and the second $pK_a$. In a particular embodiment, the pH may be equal to a $pK_a$ unit that is about equidistant between the first $pK_a$ and the second $pK_a$.

In certain embodiments, nucleic acid-hydrophobic counter ion(s) complex can occur during or after emulsification, e.g., as a result of equilibrium conditions in the fine emulsion. Without wishing to be bound by any theory, it is believed that organic-soluble counter ions (i.e., the hydrophobic counter ion agent, such as an endo-lysosomal disrupting agent) can facilitate diffusion of a hydrophilic therapeutic agent (nucleic acid) into a nanoparticle, organic phase, or droplet of an emulsion as a result of nucleic acid-hydrophobic counter ion(s) complex. Without wishing to be bound by any theory, the nucleic acid-hydrophobic counter ion(s) complex may remain in the nanoparticle, organic phase, or droplet before solidification of the nanoparticle since the solubility of the nucleic acid-hydrophobic counter ion(s) complex in the nanoparticle is higher than the solubility of the nucleic acid-hydrophobic counter ion(s) complex in the emulsion and/or in the quench. For example, by selecting a pH for the quench that is between the $pK_a$ of the nucleic acid, and the $pK_a$ of the hydrophobic counter ion agent, such as an endo-lysosomal disrupting agent, formation of nucleic acid-hydrophobic counter ion(s) complex, can be optimized. However, selecting a pH that is too high may tend to cause the hydrophobic counter ion agent, such as an endo-lysosomal disrupting agent, to diffuse out of the nanoparticle, whereas selecting a pH that is too low may tend to cause the therapeutic agent (nucleic acid) to diffuse out of the nanoparticle.

In some embodiments, the pH of an aqueous solution used in a nanoparticle formulation process (e.g., including, but not limited to, the aqueous phase, the emulsion phase, the quench, and the quenched phase) may be independently selected and may be between about 1 and about 3, in some embodiments between about 2 and about 4, in some embodiments between about 3 and about 5, in some embodiments between about 4 and about 6, in some embodiments between about 5 and about 7, in some embodiments between about 6 and about 8, in some embodiments between about 7 and about 9, and in some embodiments between about 8 and about 10. In certain embodiments, the pH of an aqueous solution used in a nanoparticle formulation process may be between about 3 and about 4, in some embodiments between about 4 and about 5, in some embodiments between about 5 and about 6, in some embodiments between about 6 and about 7, in some embodiments between about 7 and about 8, and in some embodiments between about 8 and about 9.

In some embodiments, not all of the nucleic acid is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, sodium cholate, diethylnitrosamine, sodium acetate, urea, glycerin, propylene glycol, glycofurol, poly(ethylene)glycol, bris(polyoxyethyleneglycolddodecyl ether, sodium benzoate, sodium salicylate, or combinations thereof. For example, Tween-80 may be added to the quenched nanoparticle suspension to solubilize the free drug and prevent the formation of drug crystals. In some embodiments, a ratio of drug solubilizer to the nucleic acid is about 200:1 to about 10:1, or in some embodiments about 100:1 to about 10:1.

The solubilized phase may be filtered to recover the nanoparticles. For example, ultrafiltration membranes may be used to concentrate the nanoparticle suspension and substantially eliminate organic solvent, free drug (i.e., unencapsulated nucleic acid), drug solubilizer, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g., about 0 to about 5° C., or 0 to about 10° C.) may be added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. In some embodiments, filtering may include processing about 1 to about 30, in some cases about 1 to about 15, or in some cases 1 to about 6 diavolumes. For example, filtering may include processing about 1 to about 30, or in some cases about 1 to about 6 diavolumes, at about 0 to about 5° C., and processing at least one diavolume (e.g., about 1 to about 15, about 1 to about 3, or about 1 to about 2 diavolumes) at about 20 to about 30° C. In some embodiments, filtering comprises processing different diavolumes at different distinct temperatures.

After purifying and concentrating the nanoparticle suspension, the particles may be passed through one, two or more sterilizing and/or depth filters, for example, using ~0.2 μm depth pre-filter. For example, a sterile filtration step may involve filtering the therapeutic nanoparticles using a filtration train at a controlled rate. In some embodiments, the filtration train may include a depth filter and a sterile filter.

In another embodiment of preparing nanoparticles, an organic phase is formed composed of a mixture of a nucleic acid, and polymer (e.g., a co-polymer, and optionally co-polymer with ligand). The organic phase is mixed with an aqueous phase at approximately a 1:5 ratio (oil phase: aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. In some embodiments, the quench: emulsion ratio may be about 2:1 to about 40:1, or in some embodiments about 5:1 to about 15:1. In some embodiments, the quench:emulsion ratio is approximately 8.5:1. Then a solution of Tween (e.g., Tween 80) is added to the quench to achieve approximately 2% Tween overall. This serves to dissolve free, unencapsulated nucleicacid. The nanoparticles are then isolated through either centrifugation or ultrafiltration/diafiltration.

It will be appreciated that the amounts of polymer, nucleic acid, and hydrophobic counter ion agent, such as an endo-lysosomal disrupting agent, that are used in the preparation of the formulation may differ from a final formulation. For example, some of the nucleic acid may not become completely incorporated in a nanoparticle and such free nucleic acid be e.g., filtered away. For example, in an embodiment, a first organic solution containing about 11 weight percent theoretical loading of nucleic acid in a first organic solution containing about 9% of a first hydrophobic counter ion agent, such as an endo-lysosomal disrupting agent, a second organic solution containing about 89 weight percent polymer (e.g., the polymer may include about 2.5 mol percent of a targeting moiety conjugated to a polymer and about 97.5 mol percent PLA-PEG), and an aqueous solution containing about 0.12% of a second hydrophobic counter ion agent, such as an endo-lysosomal disrupting agent, may be used in the preparation of a formulation that results in, e.g., a final nanoparticle comprising about 2 weight percent nucleic acid, about 97.5 weight percent polymer (where the polymer may include about 1.25 mol percent of a targeting moiety conjugated to a polymer and about 98.75 mol percent PLA-PEG %), and about 0.5% to about 3 total endo-lysosomal escape agent. Such processes may provide final nanoparticles suitable for administration to a patient that includes about 1 to about 20 percent by weight therapeutic agent, e.g., about 1, about 2, about 3, about 4, about 5, about 8, about 10, or about 15 percent nucleic acid by weight.

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

The pharmaceutical compositions can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbants such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing a nucleic acid agent is chosen by the individual physician in view of the patient to be treated, in general, dosage and administration are adjusted to provide an effective amount of the nucleic acid agent nanoparticle to the patient being treated. As used herein, the "effective amount" of a nanoparticle containing a nucleic acid agent refers to the amount necessary to elicit the desired biological response. As will be appreciated by those of ordinary skill in this art, the effective amount of a nanoparticle containing a nucleic acid agent may vary depending on such factors as the desired biological endpoint, the drug to be delivered, the target tissue, the route of administration, etc. For example, the effective amount of a nanoparticle containing a nucleic acid agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an embodiment, compositions disclosed herein may include less than about 10 ppm of palladium, or less than about 8 ppm, or less than about 6 ppm of palladium. For example, provided here is a composition that includes nanoparticles having a polymeric conjugate wherein the composition has less than about 10 ppm of palladium.

In some embodiments, a composition suitable for freezing is contemplated, including nanoparticles disclosed herein and a solution suitable for freezing, e.g., a sugar such as a mono, di, or poly saccharide, e.g., sucrose and/or a trehalose, and/or a salt and/or a cyclodextrin solution is added to the nanoparticle suspension. The sugar (e.g., sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w)

or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g., about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4% to about 6 wt %, e.g. about 5 wt %) sucrose and about 5 wt % to about 20% (e.g. about 7% wt percent to about 12 wt %, e.g. about 10 wt %) of a cyclodextrin, e.g., HPbCD).

The present disclosure relates in part to lyophilized pharmaceutical compositions that, when reconstituted, have a minimal amount of large aggregates. Such large aggregates may have a size greater than about 0.5 greater than about 1 or greater than about 10 and can be undesirable in a reconstituted solution. Aggregate sizes can be measured using a variety of techniques including those indicated in the U.S. Pharmacopeia at 32 <788>, hereby incorporated by reference. The tests outlined in USP 32 <788> include a light obscuration particle count test, microscopic particle count test, laser diffraction, and single particle optical sensing. In one embodiment, the particle size in a given sample is measured using laser diffraction and/or single particle optical sensing.

The USP 32 <788> by light obscuration particle count test sets forth guidelines for sampling particle sizes in a suspension. For solutions with less than or equal to 100 mL, the preparation complies with the test if the average number of particles present does not exceed 6000 per container that are ≥10 μm and 600 per container that are ≥25 μm.

As outlined in USP 32 <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 μm and 25 μm when viewed at 100× magnification. A linear scale is provided below the graticule. The number of particles with reference to 10 μm and 25 μm are visually tallied. For solutions with less than or equal to 100 mL, the preparation complies with the test if the average number of particles present does not exceed 3000 per container that are ≥10 μm and 300 per container that are ≥25 μm.

In some embodiments, a 10 mL aqueous sample of a disclosed composition upon reconstitution comprises less than 600 particles per ml having a size greater than or equal to 10 microns; and/or less than 60 particles per ml having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 μm. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,β-trehalose, α,β-trehalose, sophorose, laminaribiose, gentiobiose, turanose, maltulose, palatinose, gentiobiulose, mannobiase, melibiose, melibiulose, rutinose, rutinulose, and xylobiose. Reconstitution shows equivalent DLS size distributions when compared to the starting suspension. However, laser diffraction can detect particles of >10 μm in size in some reconstituted solutions. Further, SPOS also may detect >10 μm sized particles at a concentration above that of the FDA guidelines ($10^4$-$10^5$ particles/mL for >10 μm particles).

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, the lyophilized pharmaceutical composition may comprise about 10 to about 100 mM sodium chloride. In another embodiment, the lyophilized pharmaceutical composition may comprise about 100 to about 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used.

A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active/therapeutic agent, about 4% to about 6% (e.g. about 5% wt percent) sucrose, and about 8 to about 12 weight percent (e.g. about 10 wt. %) HPbCD.

In one aspect, a lyophilized pharmaceutical composition is provided comprising disclosed nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means such as the USP 32 <788> by light obscuration particle count test, the USP 32 <788> by microscopic particle count test, laser diffraction, and single particle optical sensing.

In an aspect, a pharmaceutical composition suitable for parenteral use upon reconstitution is provided comprising a plurality of therapeutic particles each comprising a copolymer having a hydrophobic polymer segment and a hydrophilic polymer segment; an active agent; a sugar; and a cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

In another aspect, a method of preventing substantial aggregation of particles in a pharmaceutical nanoparticle composition is provided comprising adding a sugar and a salt to the lyophilized formulation to prevent aggregation of the nanoparticles upon reconstitution. In an embodiment, a cyclodextrin is also added to the lyophilized formulation. In yet another aspect, a method of preventing substantial aggregation of particles in a pharmaceutical nanoparticle composition is provided comprising adding a sugar and a cyclodextrin to the lyophilized formulation to prevent aggregation of the nanoparticles upon reconstitution.

A contemplated lyophilized composition may have a therapeutic particle concentration of greater than about 40 mg/mL. The formulation suitable for parenteral administration may have less than about 600 particles having a size greater than 10 microns in a 10 mL dose. Lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

Methods of Treatment

In some embodiments, disclosed nanoparticles may be used to treat, alleviate, ameliorate, relieve, delay onset of, inhibit progression of, reduce severity of, and/or reduce incidence of one or more symptoms or features of a disease, disorder, and/or condition. In some embodiments, disclosed nanoparticles may be used to treat solid tumors, e.g., cancer and/or cancer cells. In some embodiments, EGFR expressing cells are treated. In some embodiments, solid tumors of other cancer cells expressing EGFR are treated. In certain embodiments, disclosed nanoparticles may be used to treat any cancer wherein PSMA is expressed on the surface of cancer cells or in the tumor neovasculature in a subject in need thereof, including the neovasculature of prostate or non-prostate solid tumors. Examples of the PSMA-related indication include, but are not limited to, prostate cancer, breast cancer, non-small cell lung cancer, colorectal carcinoma, and glioblastoma. For example, disclosed nanoparticles, may be used to treat renal cell carcinoma. In another embodiment, disclosed nanoparticles may be used to treat kidney cancer, glioblastoma multiforme, mantle cell lymphoma, or dermal Kaposi's sarcoma.

Disclosed nanoparticles may be used to treat cancer. The term "cancer" includes pre-malignant as well as malignant cancers. Cancers include, but are not limited to, blood (e.g., chronic myelogenous leukemia, chronic myelomonocytic leukemia, Philadelphia chromosome positive acute lymphoblastic leukemia, mantle cell lymphoma), prostate, gastric cancer, oropharyngeal cancer, cervical cancer, anal cancer, gallbladder cancer, bile duct cancer, cancer of the bowel, colorectal cancer, skin cancer, e.g., melanomas or basal cell carcinomas, lung cancer (e.g., small-cell lung cancer or non-small cell lung cancer (e.g. adenocarcinoma, squamous cell carcinoma)), breast cancer, cancers of the head and neck, bronchus cancer, pancreatic cancer, urinary bladder cancer, brain or central nervous system cancer, tonsillar cancer, peripheral nervous system cancer, esophageal cancer, cancer of the oral cavity or pharynx, liver cancer (e.g., hepatocellular carcinoma), kidney cancer (e.g., renal cell carcinoma), testicular cancer, biliary tract cancer, small bowel or appendix cancer, gastrointestinal stromal tumor, salivary gland cancer, thyroid gland cancer, (e.g., follicular thyroid cancer and undifferentiated thyroid cancer) adrenal gland cancer, osteosarcoma, chondrosarcoma, cancer of hematological tissues, treating cancers with KRas mutations, treating refractory cancers, and the like. "Cancer cells" can be in the form of a tumor (i.e., a solid tumor), exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction. Disclosed nanoparticles may be used to treat the physical symptoms of cancer.

In one aspect, a method for the treatment of cancer (e.g., leukemia) is provided. It should be appreciated that that other methods of treatments, such as infection, inflammation, genetic disorders, etc., can be accomplished as disclosed herein. In some embodiments, the treatment of cancer comprises administering a therapeutically effective amount of disclosed nanoparticles to a subject in need thereof, in such amounts and for such time as is necessary to achieve the desired result. In certain embodiments, a "therapeutically effective amount" of disclosed nanoparticles is that amount effective for treating, alleviating, ameliorating, relieving, delaying onset of, inhibiting progression of, reducing severity of, and/or reducing incidence of one or more symptoms or features of cancer.

In one aspect, a method for administering compositions to a subject suffering from cancer (e.g., leukemia) is provided. In some embodiments, particles may be administered to a subject in such amounts and for such time as is necessary to achieve the desired result (i.e., treatment of cancer). In certain embodiments, a "therapeutically effective amount" of particle disclosed nanoparticle is that amount effective for treating, alleviating, ameliorating, relieving, delaying onset of, inhibiting progression of, reducing severity of, and/or reducing incidence of one or more symptoms or features of cancer.

Also contemplated here are methods of treating patients that have been subject to organ transplantation, by administering disclosed nanoparticles. Other methods contemplated herein include methods of treating patients having tuberous sclerosis complex, and/or autism by administering an effective amount of a disclosed nanoparticle.

Methods contemplated herein include, for example, a method of preventing or deterring neointimal hyperplasia in a blood vessel of a patient, for example, a patient receiving a bare metal stent in a lesion of the blood vessel, is disclosed, comprising administering a composition comprising disclosed nanoparticles. Also contemplated herein are methods of treating or preventing restenosis (e.g. in a patient receiving a stent) comprising administering disclosed nanoparticles.

Contemplated methods comprise treating inflammatory diseases, which may be inflammatory bowel disease, such as Crohn's disease, ulcerative colitis, collagenous colitis, lymphocytic colitis, ischemic colitis, diversion colitis, Behcet's disease, or indeterminate colitis. In other embodiments, a method of treating irritable bowel syndrome in a patient in need thereof is provided. The method comprises administering to the patient a therapeutically effective amount of nanoparticles. In some embodiments, the nanoparticles may contain a therapeutic agent. For example, in certain embodiments, the therapeutic agent may be an anti-inflammatory agent, such as described above.

Therapeutic protocols involve administering a therapeutically effective amount of a disclosed nanoparticle to a healthy individual (i.e., a subject who does not display any symptoms of cancer and/or who has not been diagnosed with cancer). For example, healthy individuals may be "immunized" with a disclosed nanoparticle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive treatment at any time.

In other embodiments, disclosed nanoparticles can be used to inhibit the growth of cancer cells, e.g., myelogenous leukemia cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e., not as a disclosed nanoparticle).

U.S. Pat. No. 8,206,747, issued Jun. 26, 2012, entitled "Drug Loaded Polymeric Nanoparticles and Methods of Making and Using Same" is hereby incorporated by reference in its entirety.

EXAMPLES

The disclosed nanoparticles now being generally described, it will be more readily understood by reference to the following examples which are included merely for purposes of illustration of certain aspects and embodiments of the disclosed nanoparticles, and are not intended to limit the disclosed nanoparticles in any way.

Example 1: Preparation of PLA-PEG

The synthesis is accomplished by ring opening polymerization of d,l-lactide with α-hydroxy-ω-methoxypoly(ethylene glycol) as the macro-initiator, and performed at an elevated temperature using Tin (II) 2-Ethyl hexanoate as a catalyst, as shown below (PEG Mn≈5,000 Da; PLA Mn≈16,000 Da; PEG-PLA $M_n$≈21,000 Da)

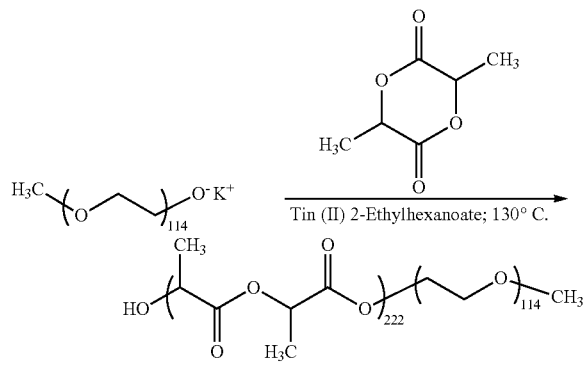

The polymer is purified by dissolving the polymer in dichloromethane, and precipitating it in a mixture of hexane and diethyl ether. The polymer recovered from this step shall be dried in an oven.

Example 2: Emulsion Process

Figure 4:
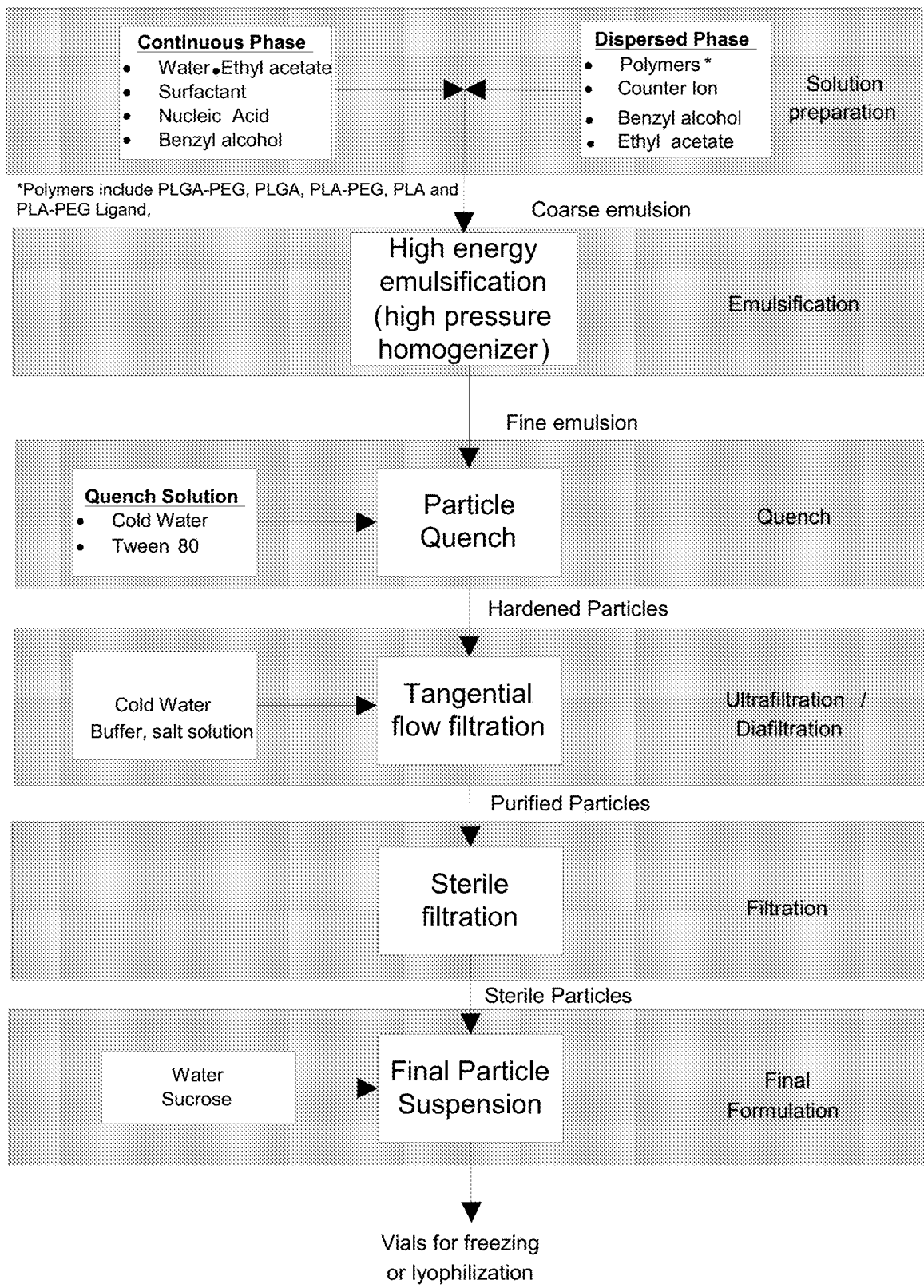
FIG. 4 is a flow chart for an emulsion process for forming disclosed nanoparticles.

A general flow chart of the process is depicted in FIG. 4. By reducing the solvent content of the emulsified oil phase, less drug is lost to the quench fluid when the nanoparticles are hardened. A solvent system is chosen having a suitable solvating power to keep the drug in solution at high concentrations. Use of a co-solvent system (typically 79:21 ethyl acetate:benzyl alcohol) allows for a continuous solution up to 50% solids (typically 20-30%, or 20-25%) with an 80:20 polymer:counter ion blend.

An organic phase is formed composed of a mixture of counter ion and polymer (co-polymer, and optionally co-polymer with ligand). The organic phase is mixed with an aqueous phase at approximately a 1:5 ratio (oil phase: aqueous phase) where the aqueous phase is composed of nucleic acid, surfactant and some dissolved solvent. In order to achieve high drug loading, about 30% solids in the organic phase is used.

The organic phase is mixed with an aqueous phase at approximately a 1:5 ratio (oil phase:aqueous phase) where the aqueous phase includes nucleic acid, optional surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water or buffer, or salt solution, at a given temperature (listed on table) under mixing. The quench: emulsion ratio is approximately 8:1. Then a solution of 25% (wt %) of Tween 80 is added to the quench to achieve approximately 2% Tween 80 overall. This serves to dissolve free, unencapsulated drug, and makes the nanoparticle isolation process feasible. The nanoparticles are then isolated through either centrifugation or ultrafiltration/diafiltration.

Example 3: Nanoparticle Preparation—Emulsion Process 2

An organic phase is formed composed of a mixture of counter ion (in some embodiments, a hydrophobic salt of a nucleic acid formed through a charge association of a cationic counter ion and the oligonucleotide) and polymer (co-polymer, and optionally co-polymer with ligand). The organic phase is mixed with an aqueous phase at approximately a 1:5 ratio (oil phase:aqueous phase) where the aqueous phase is composed of nucleic acid, surfactant and some dissolved solvent. In order to achieve high nucleic acid and counter ion loading, about 30% solids in the organic phase is used.

The primary, coarse emulsion is formed by the combination of the two phases under simple mixing or through the use of a rotor stator homogenizer.

The primary emulsion is then formed into a fine emulsion through the use of a high pressure homogenizer.

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. The quench:emulsion ratio is approximately 5:1.

A solution of 35% (wt %) of Tween 80 can be added to the quench to achieve approximately 2% Tween 80 overall. After the emulsion is quenched a solution of Tween-80 can be added.

Nanoparticles were prepared using the standard procedures such as outlined above, of varing polymer molecular weights with 100% encapsulation efficiency, as depicted below. The nucleic acid was a ssDNA: 5' CGG CAA GCT GAC CCT GAA GTT (SEQ ID NO: 6).

| PLA/PEG | Size (nm) | ZP (mV) | Loading (UV) | EE |
|---------|-----------|---------|--------------|------|
| 13.1/5  | 105       | 10.7    | 10.2%        | 100% |
| 16/5    | 99        | 10.4    | 10.6%        | 100% |
| 19.2/5  | 94        | 11.1    | 10.4%        | 100% |

Example 4: Nanoparticle Preparation—Emulsion Process 3

An organic phase is formed composed of a mixture of counter ion and polymer (co-polymer, and optionally co-polymer with ligand). The organic phase is mixed with an aqueous phase at approximately a 1:5 ratio (oil phase: aqueous phase) where the aqueous phase is composed of surfactant and some dissolved solvent. In order to achieve high nucleic acid and counter ion loading, about 30% solids in the organic phase is used.

The primary, coarse emulsion is formed by the combination of the two phases under simple mixing or through the use of a rotor stator homogenizer.

The primary emulsion is then formed into a fine emulsion through the use of a high pressure homogenizer.

An aqueous solution of oligonucleotide is then added to the fine emulsion and held for a period of time to dispersion of the oligonucleotide throughout the emulsion.

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. The quench: emulsion ratio is approximately 5:1.

A solution of 35% (wt %) of Tween 80 can be added to the quench to achieve approximately 2% Tween 80 overall. After the emulsion is quenched a solution of Tween-80 can be added.

Example 5: Nanoparticle Preparation—Post Fine Emulsion (Addition of CI Followed by Addition of Oligo)

An organic phase is formed composed of polymer (co-polymer, and optionally co-polymer with ligand) dissolved in organic solvents. The organic phase is mixed with an aqueous phase at approximately a 1:5 ratio (oil phase: aqueous phase) where the aqueous phase is composed of surfactant and some dissolved solvent. About 15% solids in the organic phase is used.

The primary, coarse emulsion is formed by the combination of the two phases under simple mixing or through the use of a rotor stator homogenizer.

The primary emulsion is then formed into a fine emulsion through the use of a high pressure homogenizer.

The counter ion is added as a powder to the fine emulsion. The solution is stirred for approximately 10 min. Then the oligo (powder) is added to the stirring fine emulsion and is stirred for another approximately 10 mins.

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. The quench:emulsion ratio is approximately 5:1.

A solution of 35% (wt %) of Tween 80 is added to the quench to achieve approximately 2% Tween 80 overall. After the emulsion is quenched a solution of Tween-80 is added.

Figure 11:
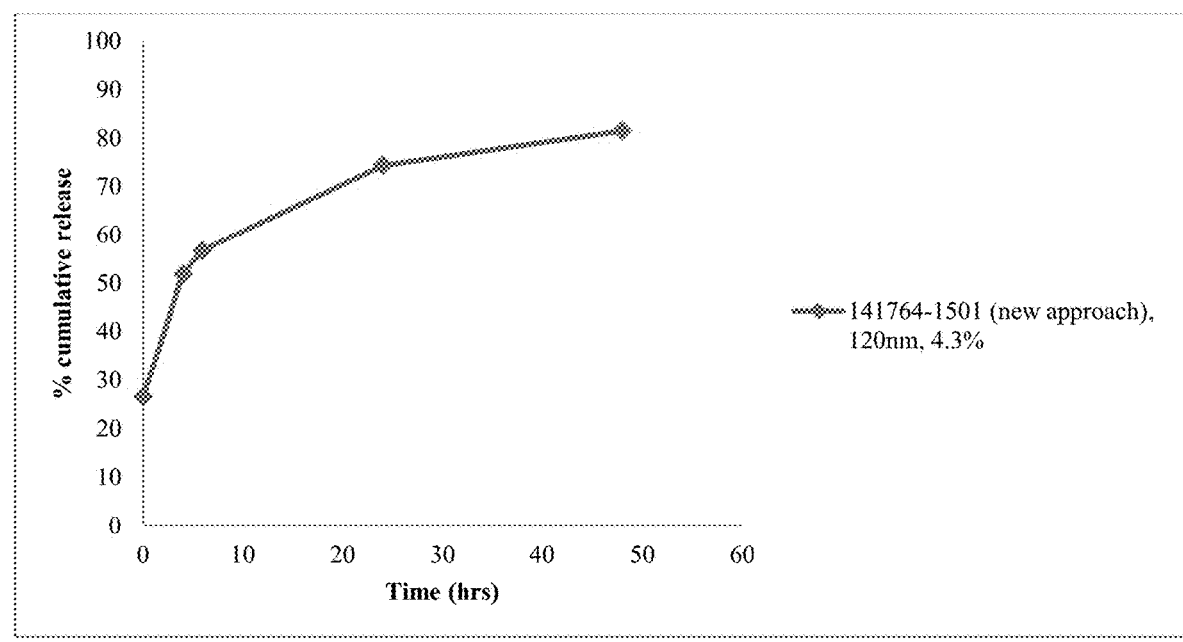
FIG. 11 depicts a release profile for nanoparticles prepared using the post fine emulsion addition of counter ion followed by addition of oligo preparation method.

Nanoparticles were prepared using the standard procedures such as outlined above. Below is the NP size, Drug load and IVR data for the batch that made with this approach. See also FIG. 11. The nucleic acid was a ssDNA: 5' CGG CAA GCT GAC CCT GAA GTT (SEQ ID NO: 6).

| PLA/PEG | Size (nm) | Loading | EE |
|---|---|---|---|
| 16/5 | 122 | 4.3 | 43% |

Example 6: In Vitro Release

An in vitro release method is used to determine the initial burst phase release from nanoparticles at both ambient and 37° C. conditions. In order to maintain sink conditions and prevent nanoparticles from entering the release samples, a dialysis system was designed. After obtaining an ultracentrifuge capable of pelleting 100 nm particles, the dialysis membranes were eliminated and centrifugation was used to separate released drug from encapsulated drug.

The dialysis system is as follows: 3 mL slurry of oligonucleotide nanoparticles (approx 250 µg/mL nucleic acid/ PLA nanoparticles, corresponding to 2.5 mg/mL solid concentration) in DI-water is placed into the inner tube of a 300 kDa MWCO dialyzer by pipetting. Instead of DI-water, a salt solution, such as NaCl, or a buffer may be used. In some embodiments a salt solution of 0.5 M NaCl is used. The nanoparticle is suspension in this media. The dialyzer is placed into a glass bottles containing 130 ml release media (2.5% hydroxyl beta cyclodextrin in PBS), which is continually stirred at 150 rpm using a shaker to prevent the formation of an unstirred water layer at the membrane/outer solution interface.

Figure 5:
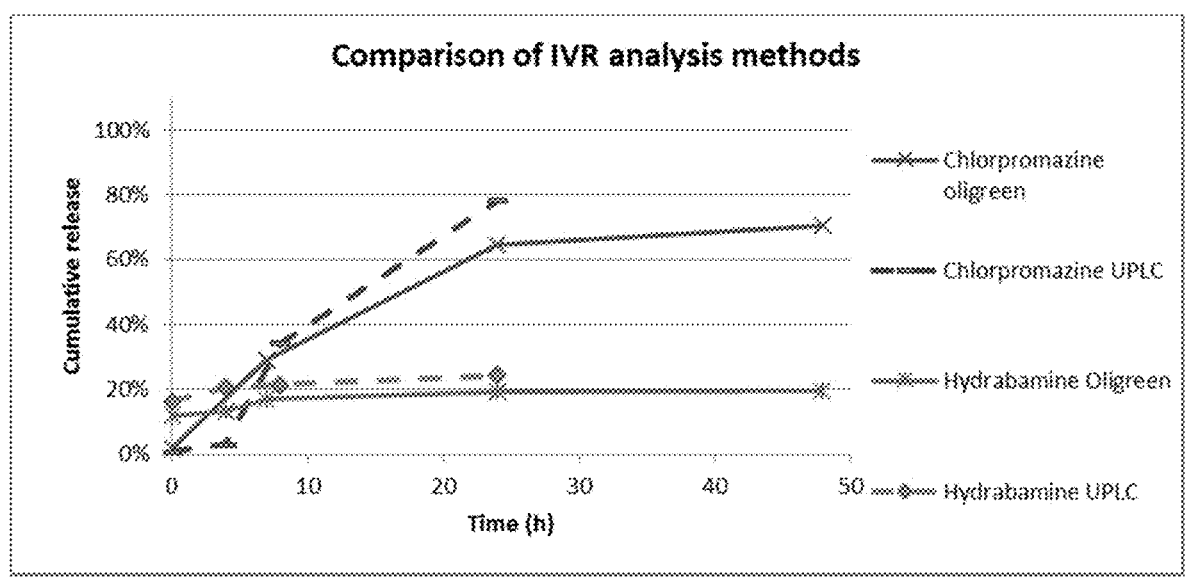
FIG. 5 depicts a comparison of the dye-based and HPLC-based quantitation for the in vitro release assay.

At pre-determined time points, aliquot of samples (1 mL) were withdrawn from the outer solution (dialysate) and analyzed for oligonucleotide concentration using dye-based methods (Oligreen). The dye-based quantiation was confirmed by HPLC. FIG. 5 depicts a comparison of dye- and HPLC-based quantitation methods used for the in vitro release.

The centrifugal system is run using similar conditions at lower suspension volumes without dialysis bags. Samples are centrifuged at 60,000 g for 30 minutes and the supernatant is assayed for drug content to measured released drug.

Example 7: Counter Ion Screening

All nucleic acid containing nanoparticles included a counter ion to enhance delivery. Counter ions tested include chlorpromazine, didodecylmethylammonium, cetylpyridinium, and hydrabamine, which were chosen based on the potential for encapsulation and control, and the ability to act as ion pairs. Nanoparticles made with varying counter ion:nucleic acid ratios were screened based on particle size, zeta potential, loading, encapsulation efficiency, and in vitro release.

Depicted below are full characterizations of the nucleic acid containing nanoparticles that include varying ratios of didodecylammonium bromide and chlorpromazine (structurally very similar to many of the endosome and lysosome disrupting molecules). Didodecylammonium bromide

| CI:oligo feed | Size (nm) | ZP (mV) | Loading (UV) | EE |
|---|---|---|---|---|
| 10 | 92 | 5.5 | 3.3% | 32% |
| 20 | 92 | 14.5 | 6.5% | 66% |
| 40 | 102 | 11.5 | 8.4% | 95% |

Chlorpromazine HCL

| CI:oligo feed | Size (nm) | ZP (mV) | Loading (UV) | EE |
|---|---|---|---|---|
| 10 | 92 | 5.5 | 3.3% | 32% |
| 20 | 92 | 14.5 | 6.5% | 66% |
| 40 | 102 | 11.5 | 8.4% | 95% |

Figure 6:
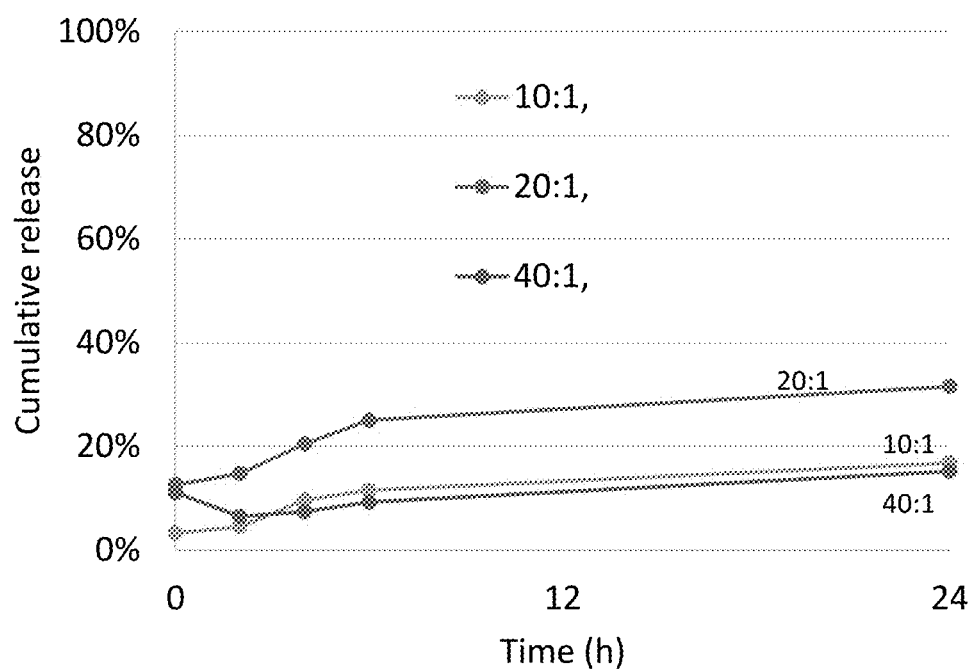
FIG. 6 depicts in vitro release of oligonucleotides over time for nanoparticles containing didodecylammonium bromide as the counter ion, or endo-lysosomal agent, at the indicated counterion agent to oligonucleotide ratio.
Figure 7:
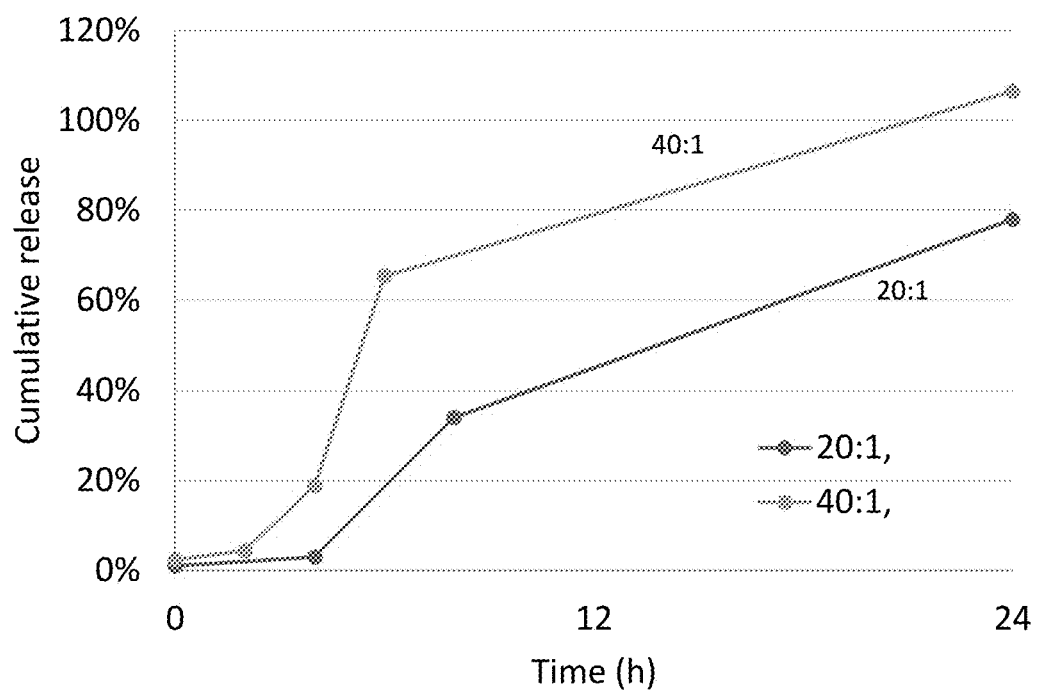
FIG. 7 depicts in vitro release of oligonucleotides over time for nanoparticles containing chlorpromazine as the counter ion, or endo-lysosomal agent, at the indicated counterion agent to oligonucleotide ratio.

FIGS. 6 and 7 show in vitro release results for nucleic acid containing nanoparticles that include varying ratios of didodecylammonium bromide and chlorpromazine, respectively.

Figure 3:
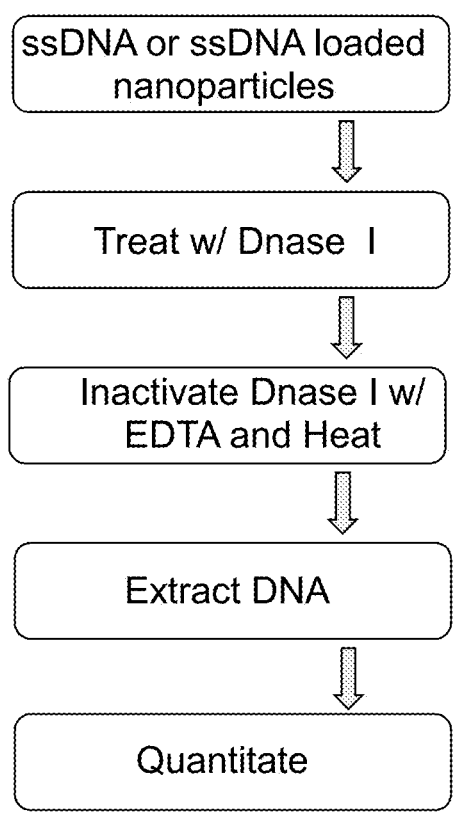
FIG. 3 is a flow chart for a nucleic acid (such as ssDNA) nuclease stability assay.
Figure 8:
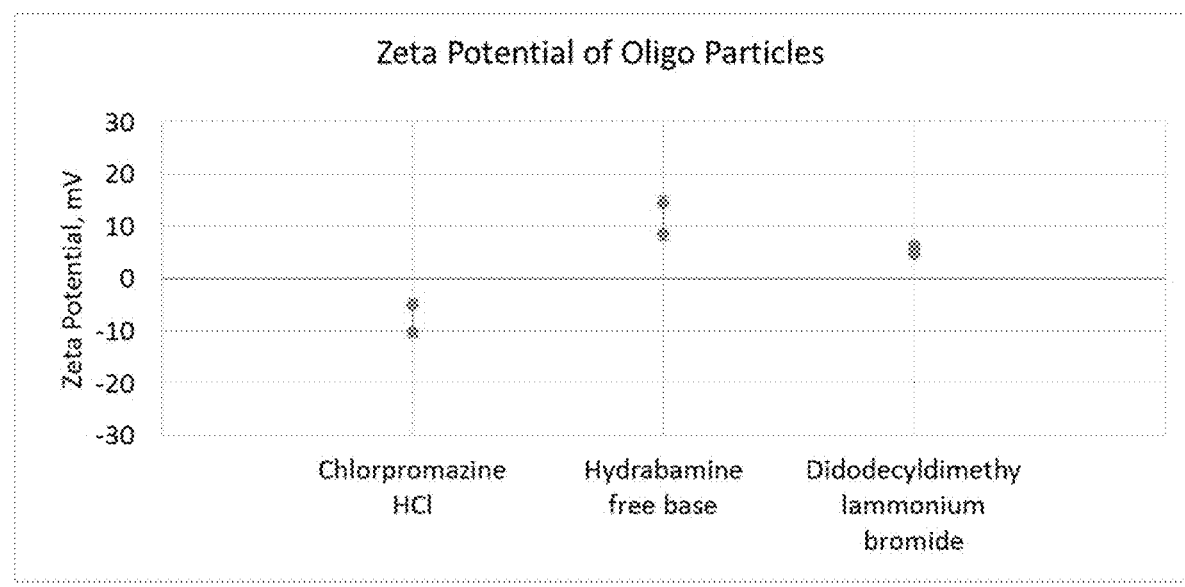
FIG. 8 depicts the zeta potential for nanoparticles loaded with nucleic acid and the indicated counter ion, or endo-lysosomal escape agent.
Figure 9:
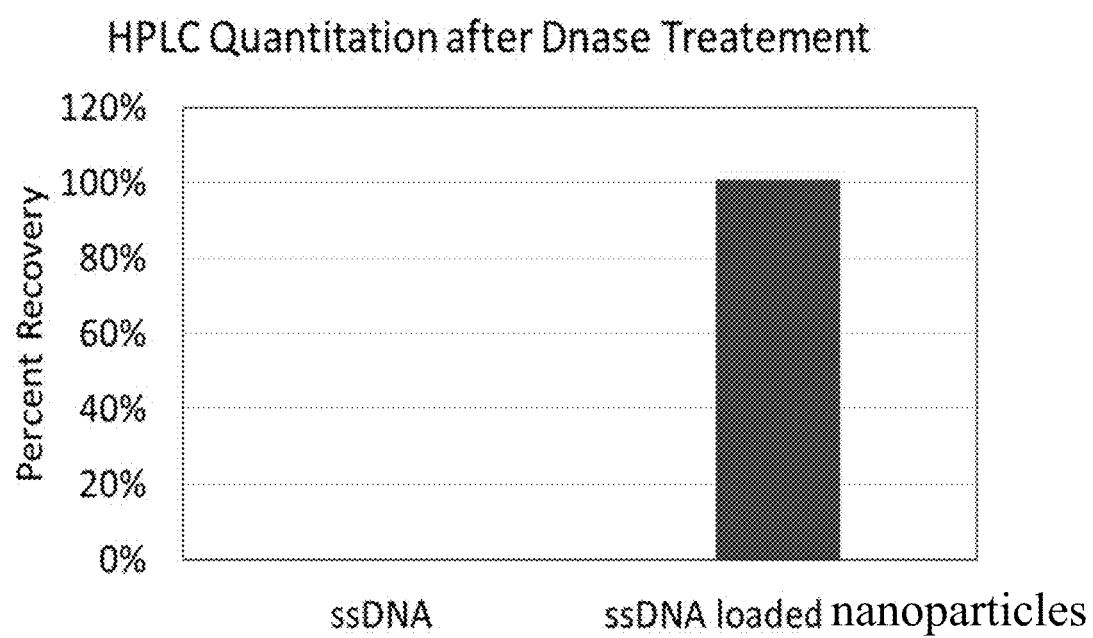
FIG. 9 depicts the stability to nuclease degradation of ssDNA encapsulated in nanoparticles relative to naked ssDNA.

FIG. 8 depicts the zeta potential of nucleic acid containing particles with the indicated counter ion. All of the particle properties appear in line with the desired neutral to slightly negative charge. As shown in FIG. 3, free ssDNA (e.g., any type DNA not in a nanoparticle) and ssDNA loaded in nanoparticles are treated with Dnase I, followed by inactivation of Dnase I. The DNA within the nanoparticles is protected from degradation, while the free nanoparticles are degraded (as shown in FIG. 9).

Example 8: Nuclease Stability of Encapsulated Material

Stability of encapsulated nucleic acid to nuclease degradation was assesed by protection from cleavage by DNaseI. Naked ssDNA or ssDNA loaded nanoparticles were treated with DNaseI, and DNA was quantitated using HPLC following DNase inactivation and DNA extraction. FIG. 9 depicts complete protection of ssDNA from proteolytic cleavage when incorporated into the indicated nanoparticles.

Example 9: In Vitro Release and Loading, or Theoretical Load

Nanoparticles containing oligonucleotides and counter ions (in a 2:1 counter ion:oligo ratio) were investigated to determine release profiles using surrogate ssDNA. See Example 6 above for methodologies. Any surrogate DNA or ssDNA or could be used (e.g., Flavin adenine dinucleotide (FAD)). The particles ranged in size from 95-100 nm. The release profiles for two counterions, ethyl lauroyl arginate and leelamine were investigated at 37° C.

Figure 12:
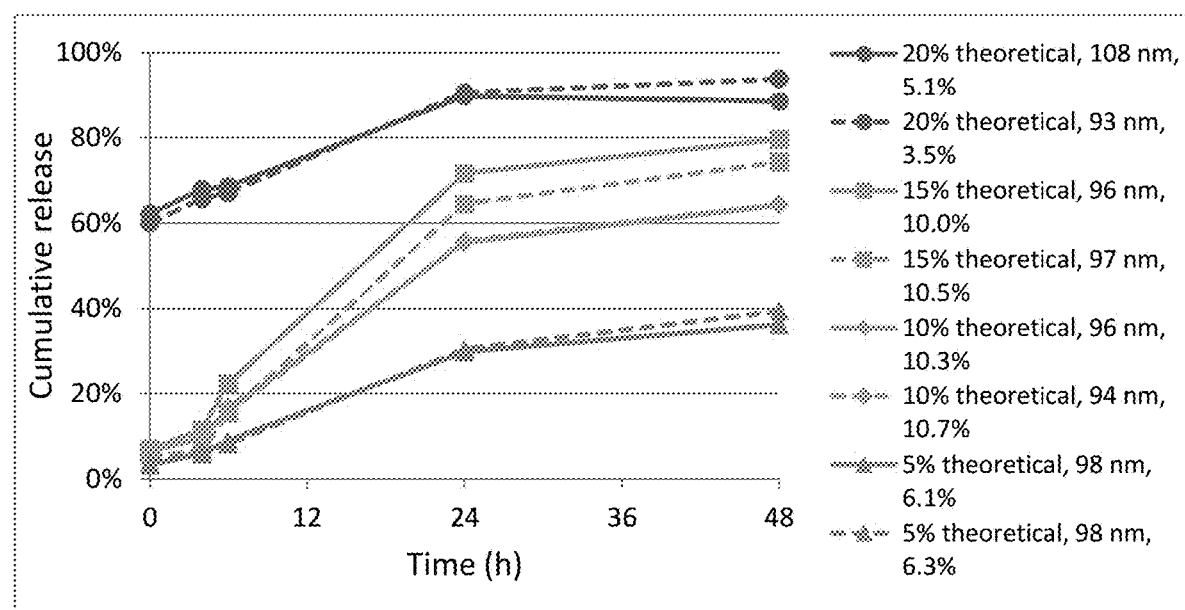
FIG. 12 depicts in vitro release of oligonucleotides over time for nanoparticles containing ethyl lauroyl arginate as the counter ion, at the indicated counterion agent to oligonucleotide ratio.

FIG. 12 depicts in vitro release profiles of oligonucleotides over time for nanoparticles containing ethyl lauroyl arginate as the counter ion for various theoretical loads.

Figure 13:
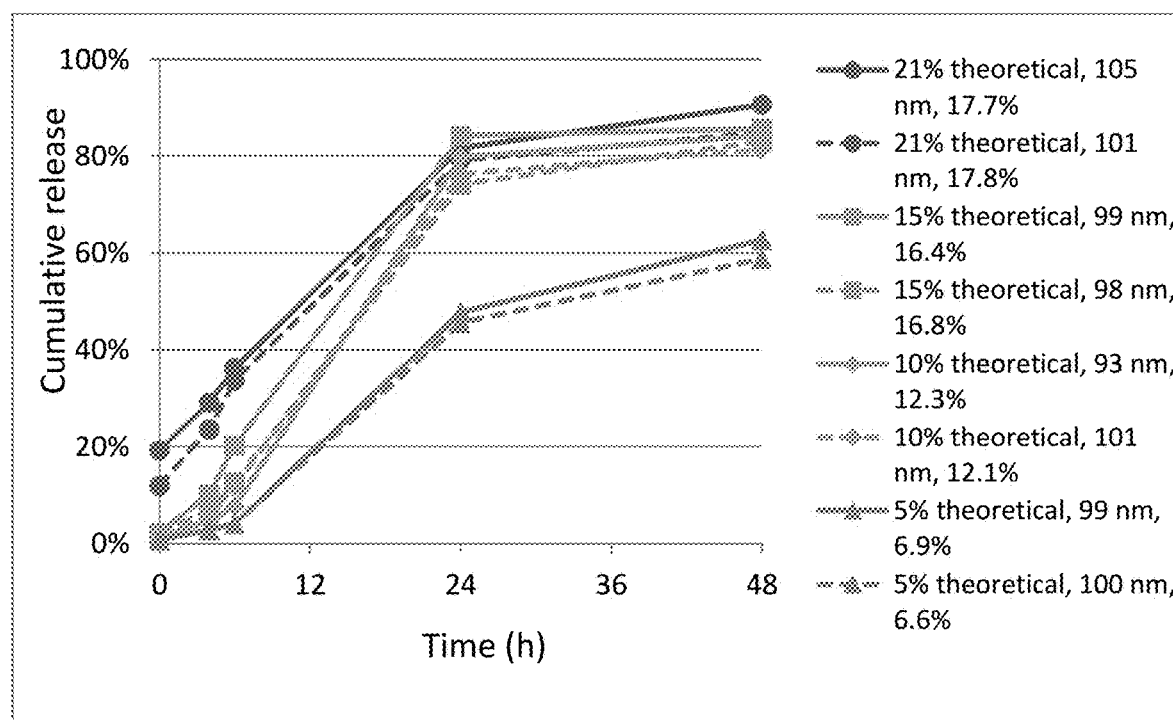
FIG. 13 depicts in vitro release of oligonucleotides over time for nanoparticles containing leelamine as the counter ion, at the indicated counterion agent to oligonucleotide ratio.

FIG. 13 depicts in vitro release of oligonucleotides over time for nanoparticles containing leelamine (endosomal escape agent) as the counter ion for various theoretical loads.

As shown in FIGS. 12 and 13, loading (or theoretical load) was observed to impact IVR without negatively impacting other attributes.

Example 10: Antisense Oligonucleotides (ASO)

Nanoparticles containing an antisense oligonucleotide (10 nucleotide RNase H domain flanked by 5 nucleotide 2'O-Me modified regions) with a counter ion (chlorpromazine) were investigated to determine release profiles. Formulations were the same as previously evaluated for ssDNA.

Figure 14:
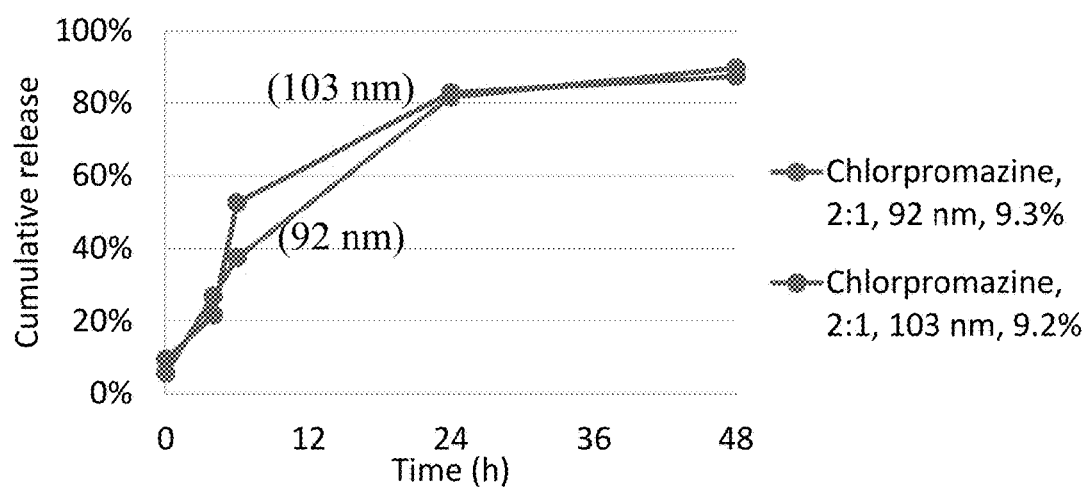
FIG. 14 depicts the release profile for an ASO-counter ion nanoparticle.

FIG. 14 depicts the release profile for nanoparticles comprising ASO and counter ions (chlorpromazine) at the indicated counter ion:oligo ratio.

Example 11: Antisense Oligonucleotides (ASO) and

Nanoparticles containing a STAT3 (signal transducer and activator of transcription 3) antisense oligonucleotide (referred to herein as STAT3 ASO) paired with an endosomal escape agent were investigated within cells to determine STAT3 expression. STAT3 is a transcription factor which is encoded by the STAT3 gene. Incubation of STAT3 ASO without any delivery agents results in no measurable reduction in STAT3 expression. By contrast, addition of a lipid-based delivery agent facilitates ASO uptake and subsequent STAT3 knockdown. This is consistent with what is known in the art that ASOs of this type are unable to cross the cell membrane and inhibit protein expression.

Figure 15A:
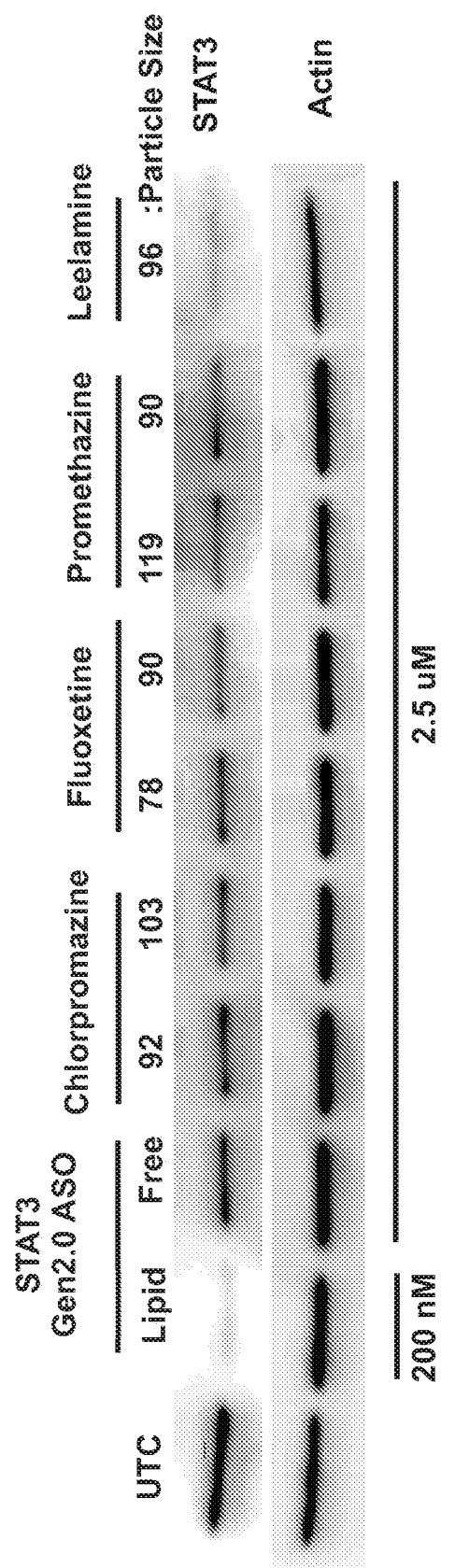
FIGS. 15A and 15B depict Western Blot results.

C4-2 cells (positive for PSMA expression) were plated at $1.5 \times 10^5$ cells per well on Day 0. It should be appreciated that C4-2 cells are commercially available, and incubating, growing and maintaining cells are well known techniques in the art. Similarly, Western Blot analysis is a well known analytical technique. On Day 1, cells were either left untreated, or were treated with 2.5 µM of STAT3 ASO (free), 200 nM of STAT3 ASO in Oligofectamine (lipid), or nanoparticles containing 2.5 µM of STAT3 ASO with an endosomal escape agent (e.g., Chlorpromazine, Fluoxetine, Promethazine or Leelamine) in growth media. Cells were incubated at 37° C. for 72 hours, at which point they were collected in lysis buffer and analyzed for STAT3 expression via Western Blot. It should be appreciated that lysing cells in a lysing buffer is a well known technique in the art. In the experiments, Actin served as the control. The results are shown in FIG. 15A. The same experiment was repeated, except cells were treated with nanoparticles containing STAT3 ASO and either Cholorpromazine, Ethyl Lauroyl Arginate, or Leelamine at either 2.5 µM or 10 uM for 72 hours. The results are shown in FIG. 15B (UTC (untreated cells), ASO (antisense oligonucleotide), CPZ (Chloropromazine), ELA (ethyl lauroyl arginate), lipid (oligofectamine)).

As shown in the Western Blot profiles of FIG. 15A, there is a measurable knockdown of STAT3 expression when the cells are treated with nanoparticles containing STAT3 ASO and the counter-ion Leelamine (2.5 µM). As shown in FIG. 15B, higher concentrations of Leelamine (10 mM) and CPZ may also facilitate ASO delivery.

Figure 15B:
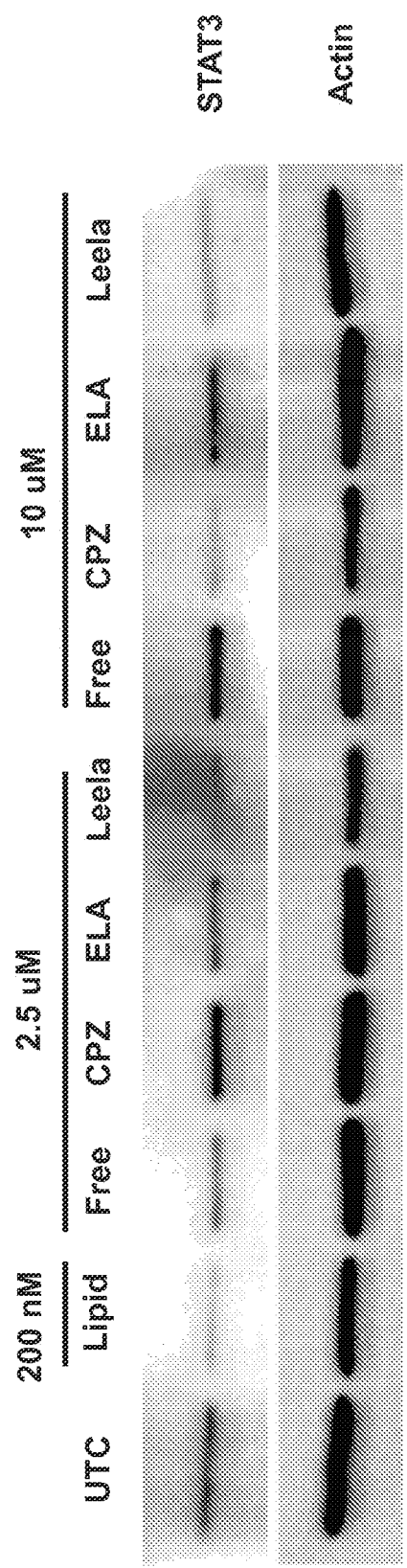

FIGS. 15A and 15B demonstrate that co-encapsulation of Leelamine with the STAT3 antisense ASO in a PSMA-targeted nanoparticle facilitates the delivery of the ASO at 2.5 and 10 µM concentrations, resulting in the knockdown of STAT3 protein expression. A similar effect is seen with Chlorpromazine-ASO at a 10 µM concentration of ASO.

Example 12: In Vitro Cell Assay

Various formulations of nanoparticles were investigated in an in vitro cell assay to determine the amount of therapeutic agent that is released from the nanoparticles and detected in the cells.

The in vitro cell assay (cellular IVR) consisted of A431 cells (epidermoid carcinoma cells) plated on a 96-well plate. Cells were seeded and incubated overnight with cell media in a $CO_2$ controlled incubator. To establish a standard curve, free ASO was 3-fold serially diluted in cell media and incubated with cells for 24 hrs. Cells were subsequently lysed and processed for cDNA synthesis followed by qPCR for mRNA levels. The following steps were performed to assess release of encapsulated ASO from nanoparticles. Nanoparticle content of encapsulated ASO was determined by HPLC analysis. Particles with known ASO content were 3-fold serially diluted in cell media on a 96-well plate and incubated at 37° C. for 24, 48 or 72 hrs. At each time point, the particles in cell media were transferred to a 96-well plate containing A431 cells along with 3-fold serially diluted free ASO (standard curve). After an additional 24 hr incubation at 37° C., cells were lysed and processed for cDNA synthesis and qPCR readout of mRNA levels. To establish the overall percent release of ASO form the nanoparticle, $IC_{50}$ levels were calculated for each nanoparticle treatment group and compared to that for free ASO.

Figure 16A:
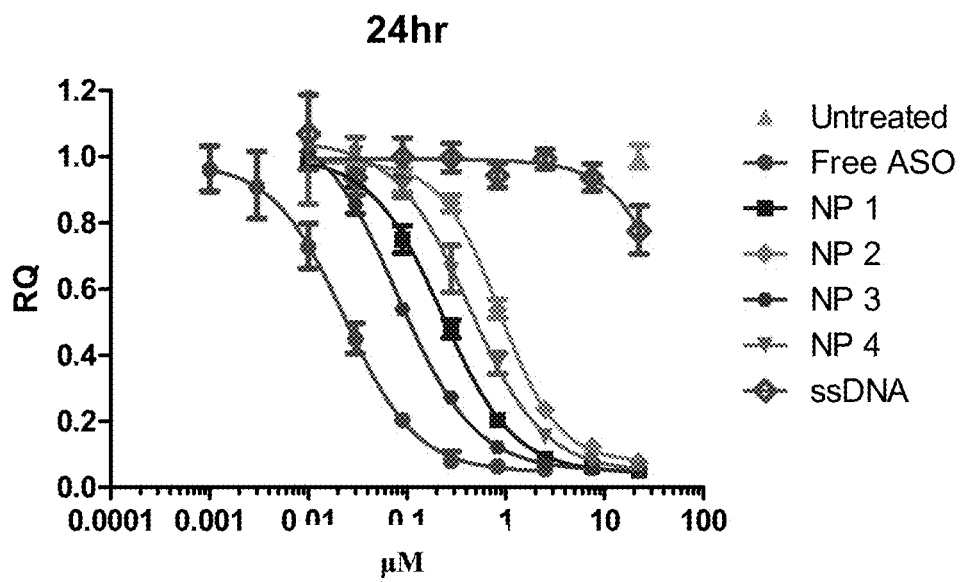
FIGS. 16A, 16B, and 16C depict the dose-response profiles for free ASO versus nanoparticle formulations 1, 2, 3, and 4 after 24, 48, or 72 hrs of ASO release from the nanoparticles.
Figure 16B:
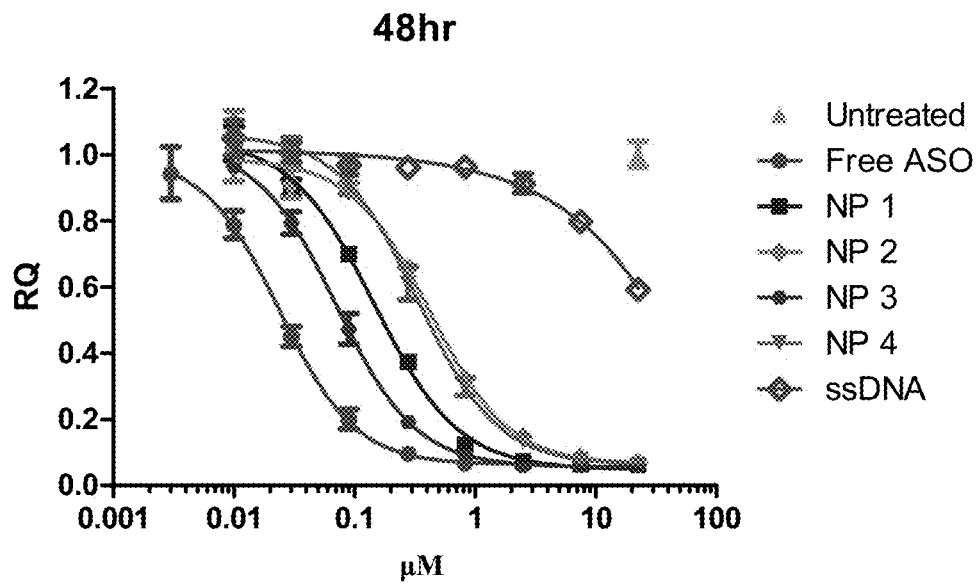
Figure 16C:
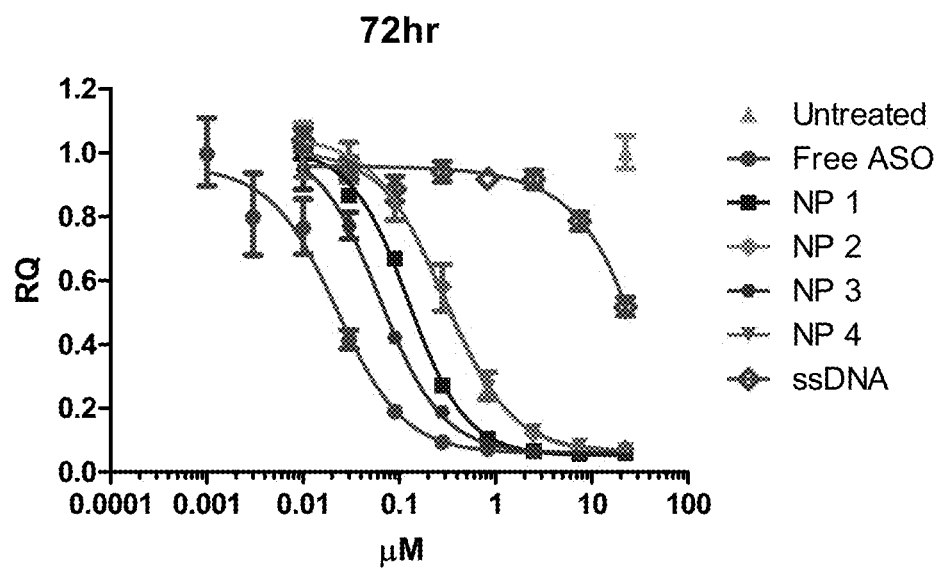
Figure 16D:
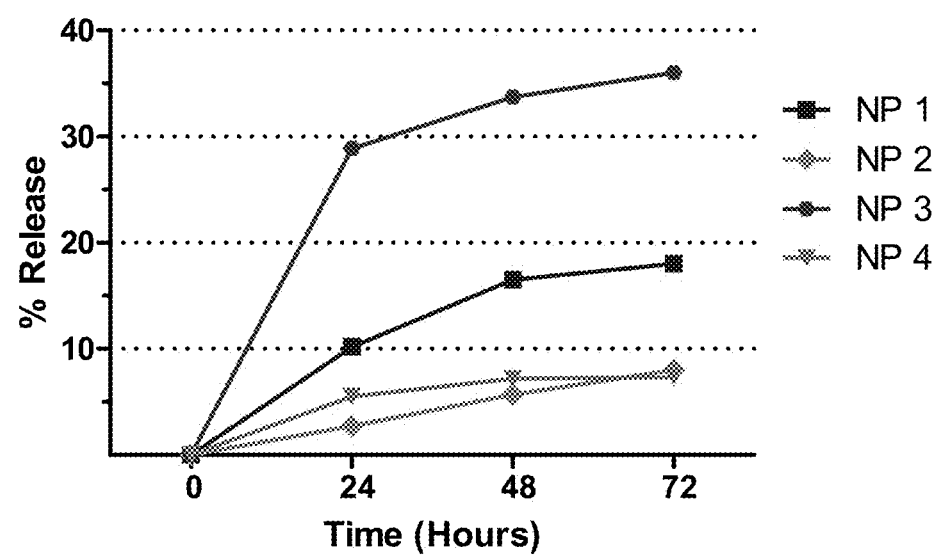
FIG. 16D depicts the $IC_{50}$ values calculated for each nanoparticle formulation relative to the free ASO treatment group which were used to calculate the relative percentage of ASO released from the nanoparticles after 24, 48 and 72 hrs of incubation at 37° C.

FIGS. 16A, 16B, and 16C depicts the dose-response profiles for free ASO versus nanoparticle formulations 1, 2, 3, and 4 after 24, 48, or 72 hrs of ASO release from the nanoparticles. The ssDNA formulation contains a non-active oligonucleotide payload as negative control. Formulation #1 is an epidermal growth factor receptor (EGFR) targeted formulation containing 10% w/w ASO payload. Formulation #2 is a non-targeted formulation containing 5% w/w ASO payload. Formulation #3 is a non-targeted formulation containing 10% w/w ASO payload. Formulation #4 is a non-targeted formulation containing 10% w/w ASO payload along with a hydrophobic excipient (HEPTAKIS 2,3,6-TRIOBENZOYL Cyclodextrin). FIG. 16D depicts the $IC_{50}$ values calculated for each nanoparticle formulation relative to the free ASO treatment group were used to calculate the relative percentage of ASO released from the nanoparticles after 24, 48 and 72 hrs of incubation at 37° C.

Figure 17A:
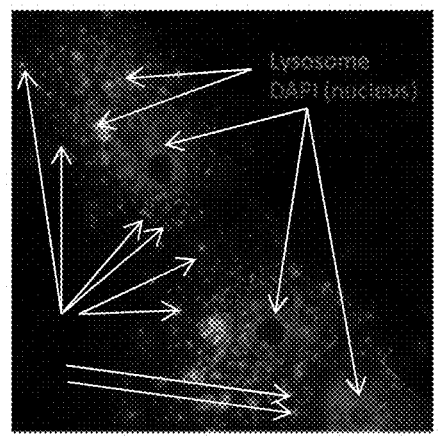
FIG. 17A depicts a fluorescence micrograph of a KB cell (epidermoid carcinoma) demonstrating the internalization and relative subcellular localization of fluorescently-labeled, folate-targeted nanoparticles (red-indicated by arrows), lysosomes (green-indicated by arrows) and the cell nucleus (blue-indicated by arrows).
Figure 17B:
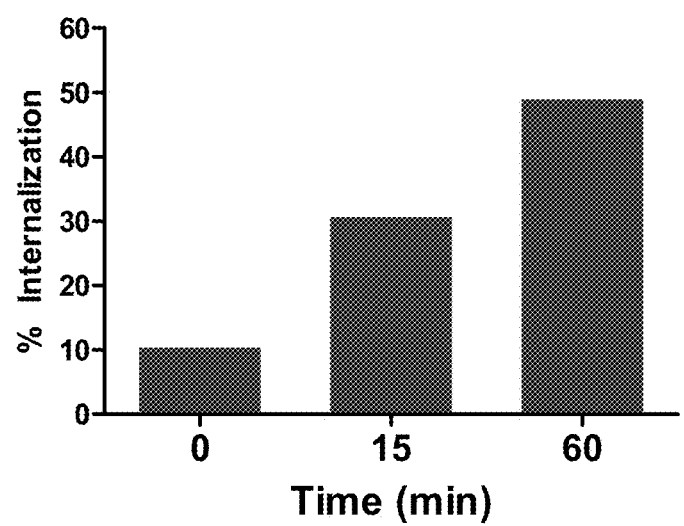
FIG. 17B depicts the percent-internalization of bound folate-targeted nanoparticle at 0 minutes, 15 minutes, and 60 minutes.

FIG. 17A depicts a fluorescence micrograph of a KB cell (epidermoid carcinoma) demonstrating the internalization and relative subcellular localization of fluorescently-labeled, folate-targeted nanoparticles (red-indicated by arrows), lysosomes (green-indicated by arrows) and the cell nucleus (blue-indicated by arrows). Three days prior to the experiment, cells were infected with a baculovirus expressing a GFP-tagged lysosomal marker. Two days later, infected KB cells were plated on glass coverslips and allowed to adhere overnight in folate-free media. The next day, the cell media was changed for new folate-free media containing folate-targeted nanoparticles, which were allowed to incubate on the cells for 60 minutes at 37° C. Cells were washed, fixed and permeabilized, stained with DAPI DNA stain, and mounted on cover slips. Images were taken at 100× magnification. FIG. 17B depicts the percent-internalization of bound folate-targeted nanoparticle at 0 minutes, 15 minutes, and 60 minutes. KB cells were collected, suspended in folate-free media containing folate-targeted fluorescent nanoparticles and incubated at 4° C. for 30 minutes. Cells were then washed to remove unbound nanoparticles, refed in folate-free media, and incubated at 37° C. for 0, 15 or 60 minutes. At each time point, the cells were collected and split into two pools. The first pool was suspended in PBS and assessed for nanoparticle fluorescence by flow cytometry—this represented total nanoparticle content (both internalized and surface bound). The second pool was resuspended in an acid wash (0.2M acetic acid, 0.5M NaCl), incubated at room temperature for 5 minutes, washed in PBS and assessed by flow cytometry. As the acid wash strips the surface-bound nanoparticles away, this fluorescent reading is a measure of only the internalized nanoparticles. Percent internalization is determined by dividing the acid washed fluorescence by the total fluorescence.

Example 13: siRNA—GFP Knockout In Vitro Cellular Assay

Nanoparticles containing a siRNA paired with an endosomal escape agent were investigated within cells to determine impact on eGFP expression. Various formulations of siRNA targeting eGFP were encapsulated in nanoparticles in A431 cellular assays. To assay for successful delivery of the siRNA payload, A431 cells stably expressing a short-lived form of eGFP containing a C-terminal PEST domain (eGFP-PEST) were plated in a 96-well tissue culture plate at 5000 cells per well the day before treatment and incubated at 37° C. with 5% humidity. The next day, media was removed and replaced with 100 ul fresh media containing the various siRNA formulations at an siRNA concentration of 2.5, 0.63 or 0.16 alone or in the presence of putative endosomal escape agents in solution, at sub-toxic doses determined previously (6.7 µM Amiodarone; 16.7 µM Amitriptyline; 50 µM Doxepin; 0.5 µM UNC-7938; 75 µM ELA.) All test groups were set up in duplicate. Cells were then incubated in the IncuCyte live-cell imaging system, where they were imaged at 10× magnification every 3 hours for a period of days. Integrated eGFP fluorescence fluorescence was averaged per field, and divided by the percent cell confluence to normalize for variations in cell density. This value was then normalized to the value of the untreated cells, which was set at 100%.

Figure 18A:
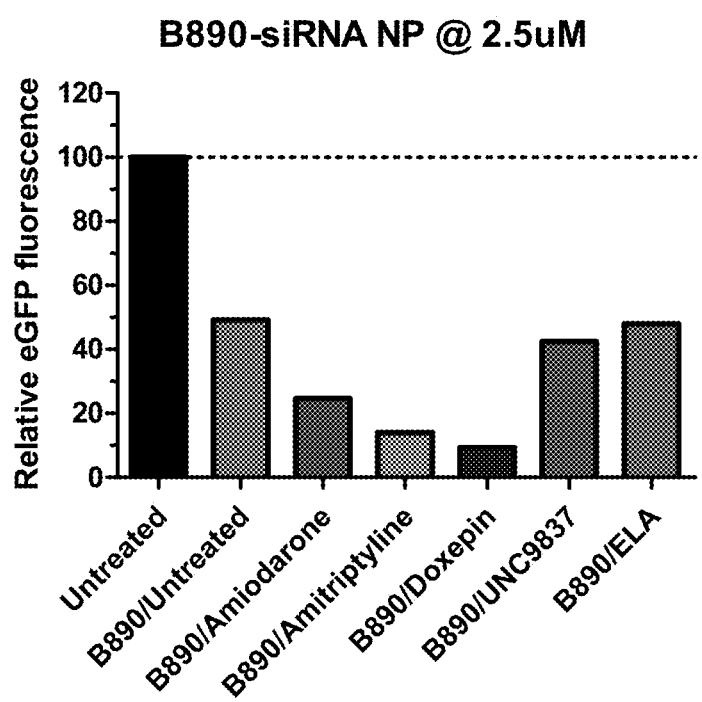
FIG. 18A and FIG. 18B depict the results for the cellular assay.
Figure 18B:
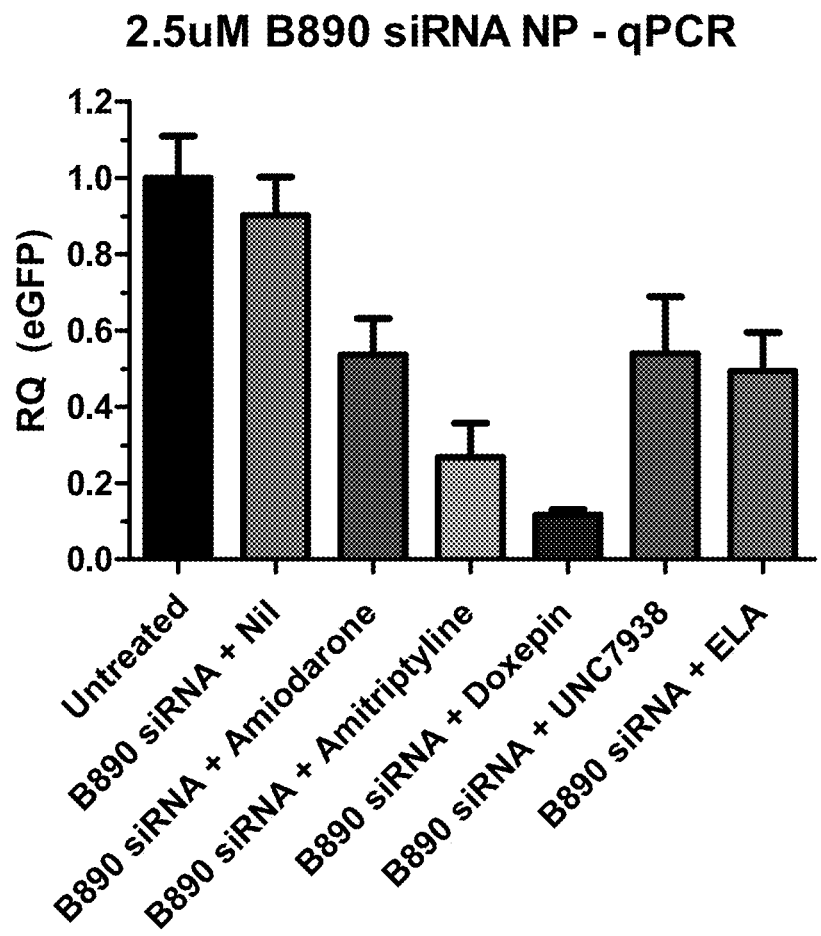

FIG. 18A and FIG. 18B depict the results for the cellular assay, in particular the relative fluorescence. FIG. 18A depicts the relative eGFP fluorescence results as measured by Incucyte® Live Cell Analysis System. FIG. 18B reports the real time PCR transcription results. As shown in FIGS. 18A and 18B, fluorescence and transcript levels generally agree. It can also be seen in the results that the fluorescence in cells exposed to the siRNA-B890 nanoparticles decreased relative to untreated cells. Similarly, siRNA-B890 nanoparticles with doxepin and amitriptyline yielded the lowest relative fluorescence.

Figure 19A:
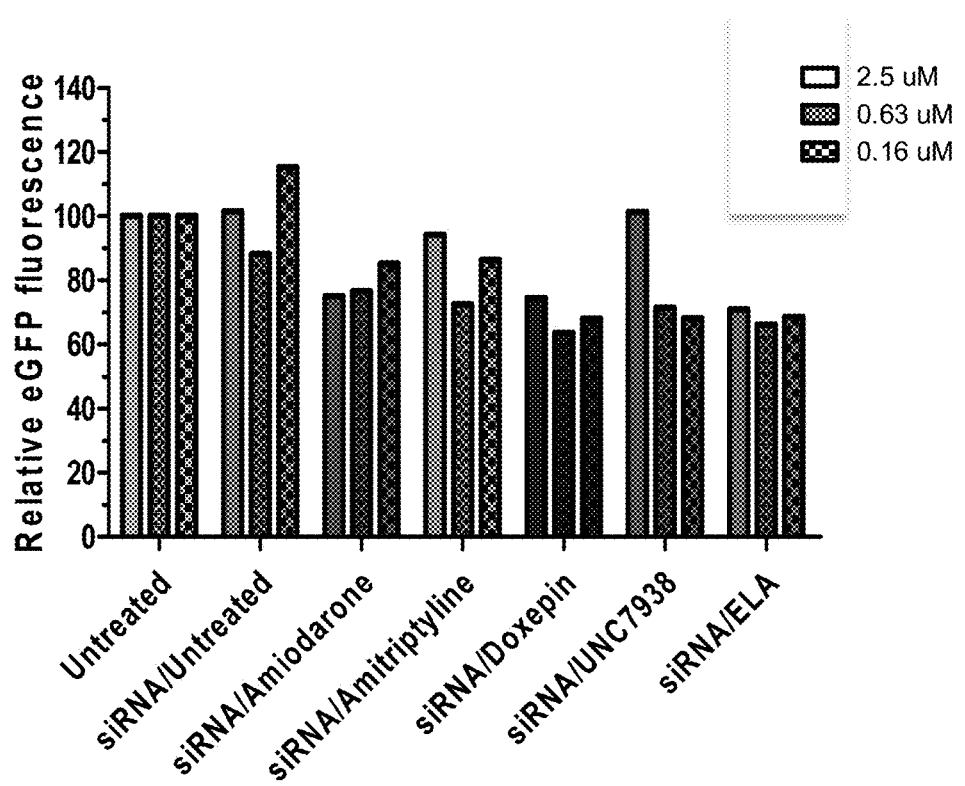
FIGS. 19A, 19B, and 19C depict the results from cellular assays conducted with free siRNA (FIG. 19A), PTNP-siRNA (FIG. 19B), and B890-siRNA (FIG. 19C).
Figure 19B:
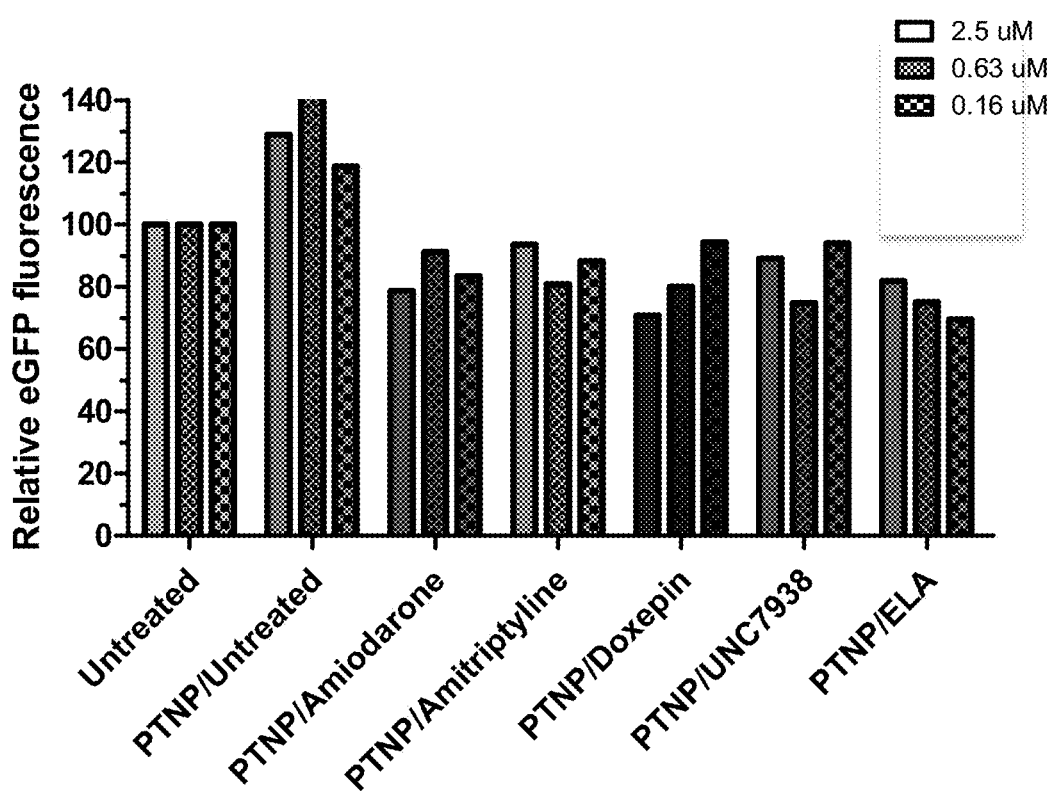
Figure 19C:
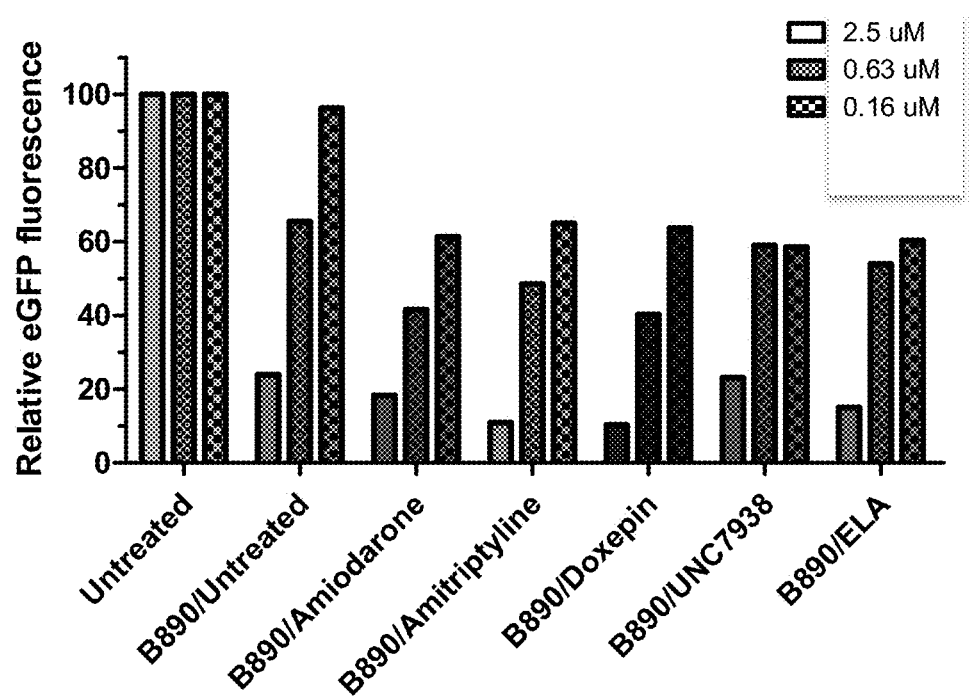

FIGS. 19A, 19B, and 19C depict the results from cellular assays as described above conducted with free siRNA (FIG. 19A), PTNP-siRNA (FIG. 19B), and B890-siRNA (FIG. 19C). PTNP indicates non-functionalized nanoparticle. As can be seen from FIGS. 19A, 19B, and 19C, B890-siRNA nanoparticles provided the lowest relative fluorescence, particularly at the 2.5 uM concentration.

Figure 20A:
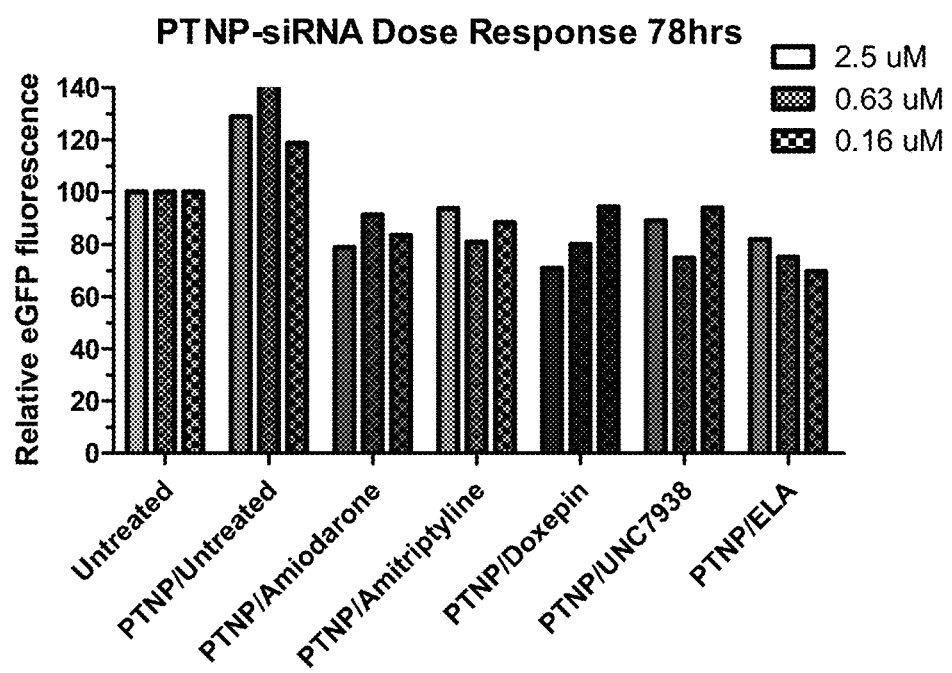
FIGS. 20A, 20B, 20C, and 20D depict the results of cellular assays at various siRNA formulations at 78 hours
Figure 20B:
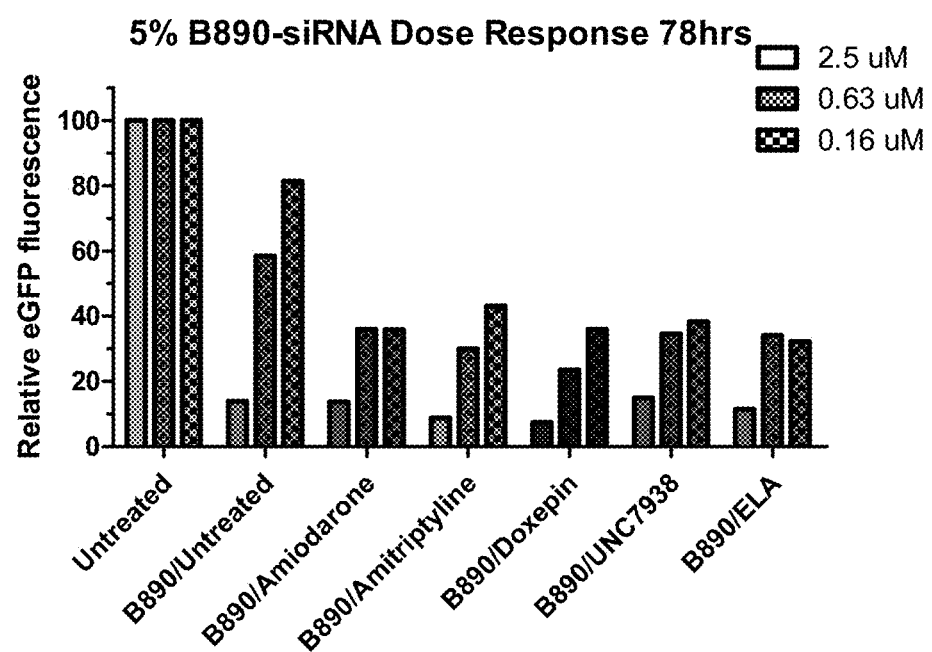
Figure 20C:
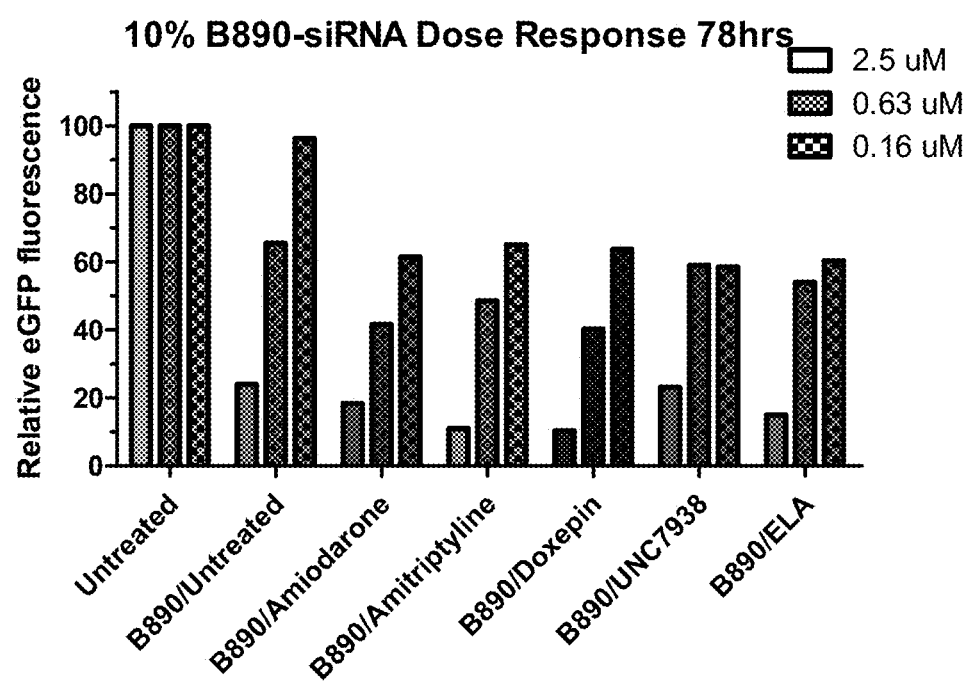
Figure 20D:
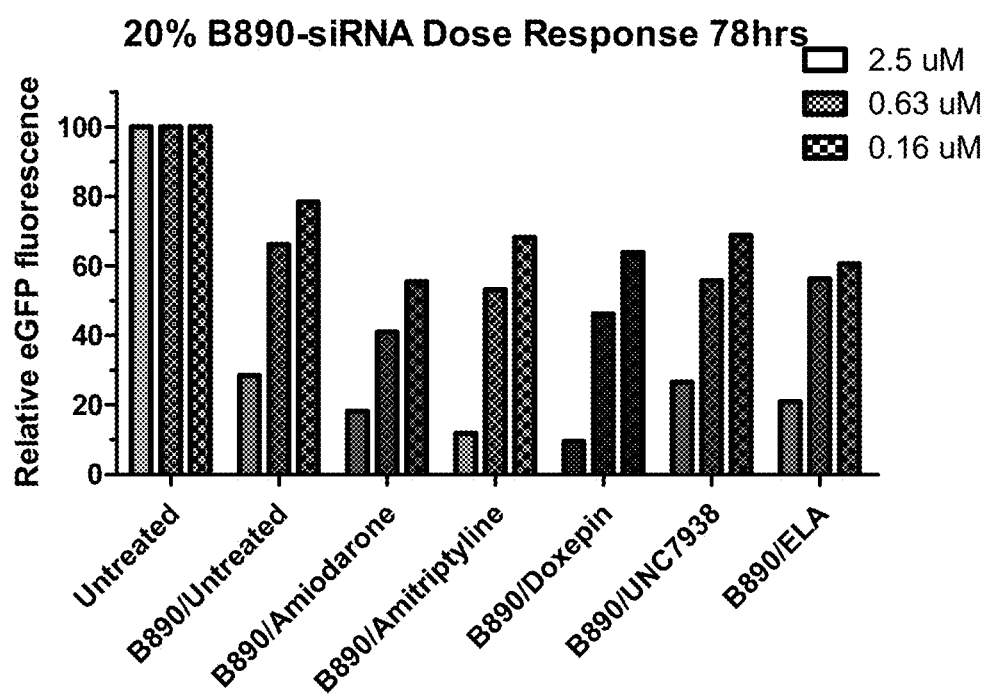

FIGS. 20A, 20B, 20C, and 20D depict the results of cellular assays at various siRNA formulations at 78 hours. FIG. 20A depicts the relative GFP fluorescence for PTNP-siRNA at 78 hours. FIG. 20B depicts the relative GFP fluorescence for 5% B890-siRNA at 78 hours. FIG. 20C depicts the relative GFP fluorescence for 10% B890-siRNA at 78 hours. FIG. 20C depicts the relative GFP fluorescence for 20% B890-siRNA at 78 hours.

Figure 21A:
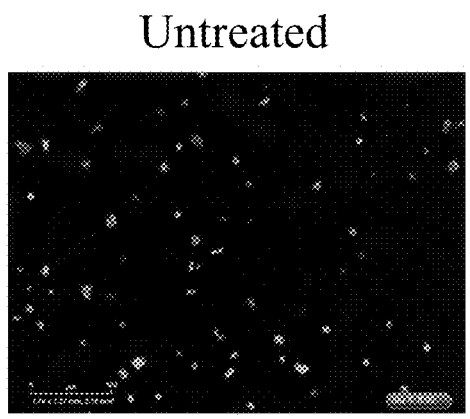
FIGS. 21A, 21B, and 21C depict the results from the cellular assay, specifically fluorescence in the cellular assay at 0 and 88 hours for untreated cells.
Figure 21B:
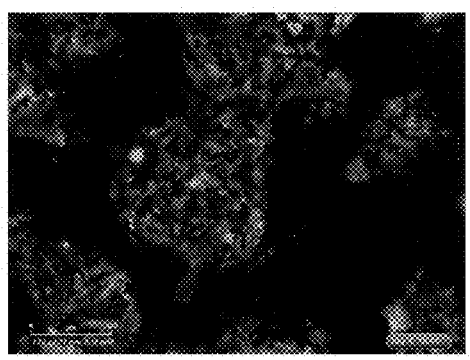
Figure 21C:
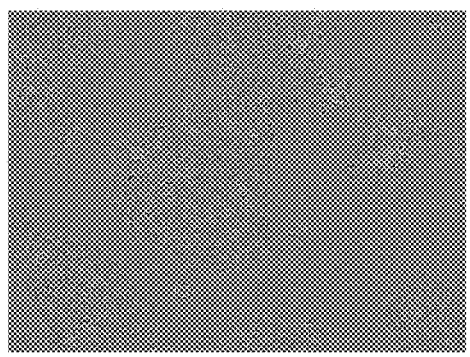
Figure 22A:
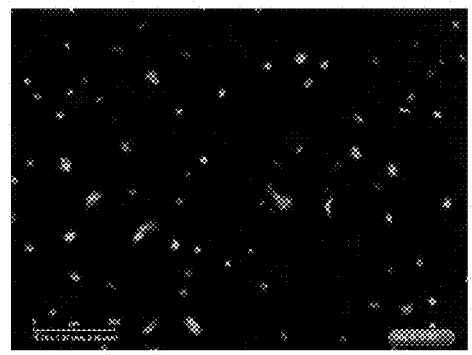
FIGS. 22A, 22B, and 22C depict the results from the cellular assay, specifically fluorescence in the cellular assay at 0 and 88 hours for B890-siRNA nanoparticles and doxepin.
Figure 22B:
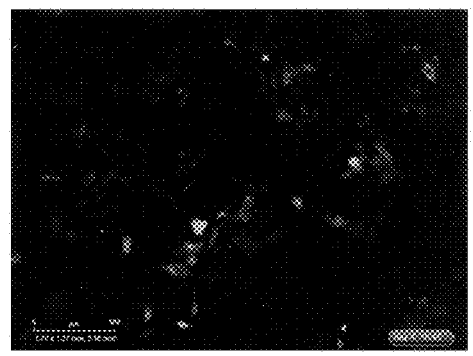
Figure 22C:
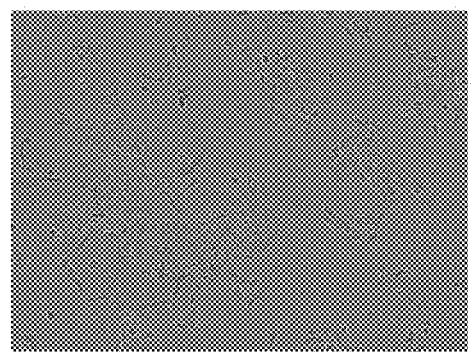

FIGS. 21A, 21B, and 21C depict the results of cellular assays, particularly fluorescence in the cellular assay at 0 and 88 hours for untreated cells, while FIGS. 22A, 22B, and 22C depict fluorescence in the cellular assay at 0 and 88 hours for B890-siRNA nanoparticles and doxepin.

EQUIVALENTS

Those skilled in the art will recognize, or be able to ascertain using no more than routine experimentation, many equivalents to the specific embodiments of the disclosed nanoparticle described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A pharmaceutically acceptable nanoparticle comprising:
   a nucleic acid and a hydrophobic counter ion agent and about 50 to about 99.75 weight percent of a diblock poly(lactic) acid-poly(ethylene)glycol copolymer or a diblock poly(lactic acid-co-glycolic acid)-poly(ethylene)glycol copolymer, wherein the counter ion is selected from the group consisting of chlorpromazine, fluoxetine, promethazine, cetylpyridinium, hydrabamine, ethyl lauroyl arginate, amitriptyline, amiodarone, and doxepin.

2. The pharmaceutically acceptable nanoparticle of claim 1, wherein the counter ion is chlorpromazine.

3. The pharmaceutically acceptable nanoparticle of claim 1, wherein the counter ion is fluoxetine.

4. The pharmaceutically acceptable nanoparticle of claim 1, wherein the counter ion is promethazine.

5. The pharmaceutically acceptable nanoparticle of claim 1, wherein the counter ion is cetylpyridinium.

6. The pharmaceutically acceptable nanoparticle of claim 1, wherein the counter ion is hydrabamine.

7. The pharmaceutically acceptable nanoparticle of claim 1, wherein the counter ion is ethyl lauroyl arginate.

8. The pharmaceutically acceptable nanoparticle of claim 1, wherein the counter ion is amitriptyline.

9. The pharmaceutically acceptable nanoparticle of claim 1, wherein the counter ion is amiodarone.

10. The pharmaceutically acceptable nanoparticle of claim 1, wherein the counter ion is doxepin.

* * * * *

SEQUENCE LISTING

<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 1

```
ctatttggat gtcagc                                                   16
```

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

```
Ala Lys Glu Arg Cys
1               5
```

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

```
Cys Arg Glu Lys Ala
1               5
```

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

```
Ala Arg Tyr Leu Gln Lys Leu Asn
1               5
```

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid

<400> SEQUENCE: 5

```
Ala Xaa Tyr Leu Xaa Xaa Leu Asn
1               5
```

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6

```
cggcaagctg accctgaagt t                                             21
```